US009665686B2

(12) United States Patent
Van Vorhis et al.

(10) Patent No.: US 9,665,686 B2
(45) Date of Patent: May 30, 2017

(54) IMPLANT PLANNING USING CORRECTED CAPTURED JOINT MOTION INFORMATION

(75) Inventors: Robert Van Vorhis, Davis, CA (US); Timothy Blackwell, Vienna, MO (US)

(73) Assignee: MAKO Surgical Corp., Fort Lauderdale, FL (US)

(*) Notice: Subject to any disclaimer, the term of this patent is extended or adjusted under 35 U.S.C. 154(b) by 983 days.

(21) Appl. No.: 12/390,046

(22) Filed: Feb. 20, 2009

(65) Prior Publication Data

US 2009/0209884 A1 Aug. 20, 2009

Related U.S. Application Data

(60) Provisional application No. 61/066,389, filed on Feb. 20, 2008.

(51) Int. Cl.
*G06F 19/00* (2011.01)
*A61F 2/38* (2006.01)
(Continued)

(52) U.S. Cl.
CPC ........ *G06F 19/34* (2013.01); *A61B 2034/101* (2016.02); *A61B 2034/2068* (2016.02); *A61F 2/38* (2013.01)

(58) Field of Classification Search
CPC ..... A61B 19/50; A61B 19/52–19/5244; A61B 19/46; A61B 17/56; A61B 2019/46–2019/469; G06F 19/3437
(Continued)

(56) References Cited

U.S. PATENT DOCUMENTS 4,823,807 A * 4/1989 Russell ................ A61B 5/1121
600/586
5,474,088 A * 12/1995 Zaharkin ................ A61B 5/103
128/897
(Continued)

FOREIGN PATENT DOCUMENTS

EP 1 800 616 6/2007
WO WO 2006/078236 7/2006
(Continued)

OTHER PUBLICATIONS

Engh, G.A., "Advances in Knee Arthroplasty for Younger Patients: Traditional Knee Arthroplasty is Prologue, the Future for Knee Arthroplasty is Prescient," Ortho SuperSite, 4 pages (2007).
(Continued)

*Primary Examiner* — Michael C Stout
(74) *Attorney, Agent, or Firm* — Foley & Lardner LLP

(57) ABSTRACT

The description relates to surgical computer systems, including computer program products, and methods for implant planning using corrected captured joint motion information. Data representative of a corrected limb pose at a plurality of poses within a range of motion of a joint associated with a particular individual is captured, the joint comprising a first bone and a second bone, while the first bone, the second bone, or both are subject to a corrective force aligning the first and second bones in a desired alignment. The first bone of the joint is represented. The second bone of the joint is represented. A first implant model is associated with the representation of the first bone. A second implant model is associated with the representation of the second bone. Based on the captured data, a relationship is determined between the first implant model and the second implant model at one or more poses of the plurality of poses within the range of
(Continued)

motion of the joint. Information representative of the determined relationship is displayed.

24 Claims, 29 Drawing Sheets

(51) Int. Cl.
*A61B 34/10* (2016.01)
*A61B 34/20* (2016.01)

(58) Field of Classification Search
USPC .............. 600/587, 595; 606/130–131, 88–89
See application file for complete search history.

(56) References Cited

U.S. PATENT DOCUMENTS

| | | | |
|---|---|---|---|
| 5,514,143 A | 5/1996 | Bonutti et al. | |
| 5,824,085 A * | 10/1998 | Sahay | A61F 2/30942 |
| | | | 128/898 |
| 6,002,859 A * | 12/1999 | DiGioia et al. | 703/11 |
| 6,205,411 B1 * | 3/2001 | DiGioia et al. | 703/11 |
| 6,361,507 B1 * | 3/2002 | Foxlin | 600/595 |
| 6,361,508 B1 * | 3/2002 | Johnson | A61B 5/1123 |
| | | | 600/595 |
| 6,585,666 B2 * | 7/2003 | Suh | A61B 5/103 |
| | | | 600/443 |
| 6,725,173 B2 * | 4/2004 | An | G01V 11/00 |
| | | | 244/3.2 |
| 6,786,877 B2 * | 9/2004 | Foxlin | 600/587 |
| 6,820,025 B2 * | 11/2004 | Bachmann | A61B 5/1114 |
| | | | 600/595 |
| 6,997,882 B1 * | 2/2006 | Parker | A61B 5/08 |
| | | | 600/301 |
| 7,089,148 B1 * | 8/2006 | Bachmann et al. | 702/151 |
| 7,104,998 B2 * | 9/2006 | Yoon | A61B 17/164 |
| | | | 606/79 |
| 2003/0176783 A1 * | 9/2003 | Hu | A61B 5/103 |
| | | | 600/429 |
| 2003/0184297 A1 * | 10/2003 | Jakab | G01R 33/285 |
| | | | 324/318 |
| 2003/0216661 A1 * | 11/2003 | Davies | A61B 5/04002 |
| | | | 600/547 |
| 2004/0006393 A1 * | 1/2004 | Burkinshaw | A61F 2/38 |
| | | | 623/20.3 |
| 2004/0019382 A1 * | 1/2004 | Amirouche | A61B 5/0031 |
| | | | 623/18.11 |
| 2004/0034313 A1 * | 2/2004 | Leitner | A61B 5/1114 |
| | | | 600/595 |
| 2004/0091140 A1 * | 5/2004 | Arakawa | G06T 7/60 |
| | | | 382/132 |
| 2004/0153079 A1 * | 8/2004 | Tsougarakis et al. | 606/77 |
| 2004/0181144 A1 * | 9/2004 | Cinquin et al. | 600/407 |
| 2005/0054917 A1 * | 3/2005 | Kitson | G06F 19/3437 |
| | | | 600/427 |
| 2005/0197814 A1 * | 9/2005 | Aram | A61F 2/30942 |
| | | | 703/11 |
| 2005/0251026 A1 * | 11/2005 | Stone | A61B 17/175 |
| | | | 600/424 |
| 2005/0251065 A1 * | 11/2005 | Henning | A61B 5/1076 |
| | | | 600/587 |
| 2005/0251148 A1 * | 11/2005 | Friedrich et al. | 606/88 |
| 2005/0267485 A1 * | 12/2005 | Cordes et al. | 606/88 |
| 2006/0004284 A1 * | 1/2006 | Grunschlager | A61B 6/00 |
| | | | 600/416 |
| 2006/0015120 A1 * | 1/2006 | Richard | A61B 19/46 |
| | | | 606/102 |
| 2006/0020177 A1 * | 1/2006 | Seo | A61B 5/222 |
| | | | 600/300 |
| 2006/0089657 A1 * | 4/2006 | Broers | A61B 5/103 |
| | | | 606/102 |
| 2006/0142657 A1 * | 6/2006 | Quaid | A61B 17/1764 |
| | | | 600/424 |
| 2006/0241640 A1 | 10/2006 | Briard et al. | |
| 2006/0270949 A1 * | 11/2006 | Mathie | A61B 5/0002 |
| | | | 600/595 |
| 2006/0282023 A1 * | 12/2006 | Leitner | A61B 5/103 |
| | | | 600/595 |
| 2007/0032748 A1 * | 2/2007 | McNeil | A61B 5/1038 |
| | | | 600/595 |
| 2007/0043287 A1 * | 2/2007 | Degraaf | 600/410 |
| 2007/0179626 A1 * | 8/2007 | de la Barrera | A61B 17/025 |
| | | | 623/20.14 |
| 2007/0219561 A1 * | 9/2007 | Lavallee | A61B 17/025 |
| | | | 606/90 |
| 2007/0226986 A1 * | 10/2007 | Park | A61B 17/155 |
| | | | 29/592 |
| 2007/0249967 A1 * | 10/2007 | Buly | A61B 5/1121 |
| | | | 600/595 |
| 2008/0010705 A1 | 1/2008 | Quaid et al. | |
| 2008/0058945 A1 * | 3/2008 | Hajaj | A61F 2/38 |
| | | | 623/20.14 |
| 2008/0162074 A1 * | 7/2008 | Schneider | A61B 19/52 |
| | | | 702/150 |
| 2008/0202200 A1 * | 8/2008 | West | A61B 6/12 |
| | | | 73/1.79 |
| 2008/0243127 A1 * | 10/2008 | Lang | A61B 17/1739 |
| | | | 606/87 |
| 2008/0262812 A1 * | 10/2008 | Arata | A61B 19/52 |
| | | | 703/11 |
| 2008/0285805 A1 * | 11/2008 | Luinge | G06F 3/011 |
| | | | 382/107 |
| 2009/0000627 A1 * | 1/2009 | Quaid et al. | 128/898 |
| 2009/0012532 A1 * | 1/2009 | Quaid et al. | 606/130 |
| 2009/0209884 A1 * | 8/2009 | Van Vorhis et al. | 600/595 |
| 2009/0270868 A1 * | 10/2009 | Park et al. | 606/87 |
| 2010/0063508 A1 * | 3/2010 | Borja | A61B 17/154 |
| | | | 606/88 |
| 2010/0113980 A1 * | 5/2010 | Herr et al. | 600/587 |
| 2010/0153076 A1 | 6/2010 | Bellettre et al. | |
| 2010/0153081 A1 * | 6/2010 | Bellettre et al. | 703/11 |
| 2010/0256504 A1 * | 10/2010 | Moreau-Gaudry | A61B 5/0066 |
| | | | 600/476 |
| 2011/0028865 A1 * | 2/2011 | Luinge et al. | 600/595 |
| 2011/0029116 A1 * | 2/2011 | Jordan | A61B 17/155 |
| | | | 700/98 |
| 2012/0172712 A1 * | 7/2012 | Bar-Tal | 600/424 |
| 2012/0203140 A1 * | 8/2012 | Malchau et al. | 600/595 |

FOREIGN PATENT DOCUMENTS

| | | |
|---|---|---|
| WO | WO 2007/064695 | 6/2007 |
| WO | WO 2007/070024 | 6/2007 |
| WO | WO 2008/130454 | 10/2008 |

OTHER PUBLICATIONS

Swank et al., "Ligament balancing in computer-assisted total knee arthroplasty: improved clinical results with a spring-loaded tensioning device," *J. Engineering in Medicine, Proc. IMechE*, 221Part H):755-761 (2007).

International Search Report and Written Opinion for International Application No. PCT/US2009/034705, Date of Mailing May 18, 2009 (15 pages).

* cited by examiner

Display Axes

Display All Implants

Angle

50—0
51—Gap: 1.2 mm

IMPLANT PLANNING USING CORRECTED CAPTURED JOINT MOTION INFORMATION

CROSS REFERENCE TO RELATED APPLICATIONS

The present application claims priority to U.S. Provisional Patent Application Ser. No. 61/066,389, filed on Feb. 20, 2008, entitled "Valgus moment method," which is hereby incorporated by reference herein in its entirety.

FIELD OF THE INVENTION

The invention relates to surgical computer systems, including computer program products, and methods for implant planning using corrected captured joint motion information.

BACKGROUND OF THE INVENTION

Orthopedic joint replacement surgery may involve arthroplasty of a knee, hip, or other joint (e.g., shoulder, elbow, wrist, ankle, finger, etc.). During joint replacement surgery, a surgeon typically removes diseased bone from the joint and replaces the resected bone with prosthetic implant components. Challenges of joint replacement surgery include determining the appropriate position for implant components within the joint relative to the bone and other implant components and accurately cutting and reshaping bone to precisely correspond to the planned placement of the implant components. Inaccurate positioning of implants may compromise joint performance and reduce implant life.

An important aspect of implant planning concerns variations in individual anatomy. Anatomical variation complicates implant planning because there is no single implant design or placement of implant components that provides an optimal solution for all patients. Implant planning is further complicated when the joint is subject to a disease state, such as osteoarthritis, that causes defects (e.g., osteophytes, capsular adhesions, osteochondral defects (OCD), and the like) that prevent the bones of the limb from achieving a desired alignment, such as a neutral alignment. For example, when a person with a healthy knee joint is in a standing position and the joint bears weight, the femur and tibia are neutrally aligned such that the center of the femoral head (i.e., the hip center), the center of the knee joint (i.e., the knee center), and the center of the ankle joint (i.e., the ankle center) are in line. This results in a neutral leg alignment (i.e., a neutral limb pose) in which the relative poses (i.e., position and/or orientation) of the femur and the tibia result in both the medial and lateral femoral condyles articulating with the tibial articular surface. In contrast, when a person has disease in one compartment of the knee joint (e.g., medial or lateral), the diseased compartment may collapse, causing the limb to adopt a non-neutral or misaligned pose.

One goal of implant planning is to determine a placement of implant components that will sufficiently correct the disease state such that proper or appropriate joint kinematics are restored. Appropriate joint kinematics may vary from person to person based on the unique anatomy of each individual. For example, appropriate joint kinematics may be achieved by planning the implant components such that, after the implants are installed, the limb is in an appropriate or desired alignment (e.g., limb alignment is restored to its pre-disease state and/or the limb will have a postoperative alignment that is neutral or near neutral for the particular patient). In conventional implant planning, a surgeon typically plans implant placement using preoperative images (e.g., CT scans) of the patient's joint. Because the disease state may prevent the limb from achieving the desired pose, however, the preoperative images may not enable the surgeon to accurately assess how the femur and tibia would move relative to one another in the desired alignment. As a result, the surgeon may have difficulty determining how to place and orient each implant component to postoperatively achieve the desired limb alignment throughout the range of motion of the joint.

Additionally, there are different philosophies for addressing the disease state, such as the restoration philosophy and the correction philosophy. The restoration philosophy, which is the prevailing philosophy, is to achieve a postoperative outcome that "restores" the leg alignment to its pre-diseased state. The correction philosophy seeks to attain a postoperative result that "corrects" the leg alignment to a predefined alignment. For example, in the restoration philosophy, the limb is aligned to properly tension the soft tissue (e.g., the ligaments). The alignment at which the soft tissues are properly tensioned is typically close to neutral but may vary for each individual based on anatomical variations. In contrast, under the correction philosophy, the leg is placed in a predefined alignment with the soft tissue being modified (as necessary) to achieve and maintain the predefined alignment. Regardless of the philosophy used by the surgeon, for a patient having disease in the medial compartment of the knee joint, the postoperative restored or corrected alignment will be less varus. Similarly, for a patient having disease in the lateral compartment, the postoperative restored or corrected alignment will be less valgus.

In view of the foregoing, a need exists for surgical methods and devices which can overcome the aforementioned problems so as to enable intraoperative implant planning for accurate placement and implantation of joint implant components, where the implant plan is customized to the patient's unique anatomy and postoperatively achieves a desired limb alignment concurrent with appropriate ligament tension throughout the range of motion of the joint.

SUMMARY OF THE INVENTION

The techniques described herein provide methods, apparatuses, and computer program products for implant planning using corrected captured joint motion information. In one aspect, there is a method. The method is a surgical planning method. The method includes capturing data representative of a corrected limb pose at a plurality of poses within a range of motion of a joint associated with a particular individual, the joint comprising a first bone and a second bone, while the first bone, the second bone, or both are subject to a corrective force aligning the first and second bones in a desired alignment. The method also includes representing the first bone of the joint and representing the second bone of the joint. The method also includes associating a first implant model with the representation of the first bone and associating a second implant model with the representation of the second bone. The method also includes, based on the captured data, determining a relationship between the first implant model and the second implant model at one or more poses of the plurality of poses within the range of motion of the joint, and displaying information representative of the determined relationship.

In one aspect, there is a system. The system is a surgical planning system. The system includes a computer configured to capture data representative of a corrected limb pose at a plurality of poses within a range of motion of a joint associated with a particular individual, the joint comprising a first bone and a second bone, while the first bone, the second bone, or both are subject to a corrective force aligning the first and second bones in a desired alignment. The computer is also configured to represent the first bone of the joint and to represent the second bone of the joint. The computer is also configured to associate a first implant model with the representation of the first bone, and to associate a second implant model with the representation of the second bone. The computer is also configured to, based on the captured data, determine a relationship between the first implant model and the second implant model at one or more poses of the plurality of poses within the range of motion of the joint, and to display information representative of the determined relationship.

In one aspect, there is a computer program product. The computer program product is tangibly embodied in a computer readable medium. The computer program product includes instructions being operable to cause a data processing apparatus to capture data representative of a corrected limb pose at a plurality of poses within a range of motion of a joint associated with a particular individual, the joint comprising a first bone and a second bone, while the first bone, the second bone, or both are subject to a corrective force aligning the first and second bones in a desired alignment. The instructions are also operable to cause a data processing apparatus to represent the first bone of the joint, and to represent the second bone of the joint. The instructions are also operable to cause a data processing apparatus to associate a first implant model with the representation of the first bone, and to associate a second implant model with the representation of the second bone. The instructions are also operable to cause a data processing apparatus to, based on the captured data, determine a relationship between the first implant model and the second implant model at one or more poses of the plurality of poses within the range of motion of the joint, and to display information representative of the determined relationship.

In one aspect, there is a system. The system includes means for capturing data representative of a corrected limb pose at a plurality of poses within a range of motion of a joint associated with a particular individual, the joint comprising a first bone and a second bone, while the first bone, the second bone, or both are subject to a corrective force aligning the first and second bones in a desired alignment. The system also includes means for representing the first bone of the joint, and means for representing the second bone of the joint. The system also includes means for associating a first implant model with the representation of the first bone, and means for associating a second implant model with the representation of the second bone. The system also includes means for, based on the captured data, determining a relationship between the first implant model and the second implant model at one or more poses of the plurality of poses within the range of motion of the joint, and means for displaying information representative of the determined relationship.

Any of the above aspects can include one or more of the following features. The desired alignment can be based on a mechanical axis of the first and second bones, an anatomic axis of the first bone, an anatomic axis of the second bone, a tension of one or more ligaments associated with the joint, or any combination thereof. The corrective force can be applied to induce a moment on the joint, the induced moment correcting a tension of one or more ligaments associated with the joint. Prior to applying the corrective force, an influence of one or more defects of the joint associated with a disease pathology can be surgically neutralized, wherein the one or more defects prevent the first and second bones from achieving the desired alignment. The disease pathology can include osteoarthritis and the one or more defects can include an osteophyte, a capsular adhesion, an osteochonral defect, or any combination thereof.

In some examples, the plurality of poses includes a full extension of the joint, a full flexion of the joint, a pose of the joint between full extension and full flexion, or any combination thereof. A corrective force of a first magnitude at a first pose of the plurality of poses can be applied to correct a tension of one or more ligaments associated with the joint, and a corrective force of a second magnitude at a second pose of the plurality of poses can be applied to correct the tension of the one or more ligaments. Displaying the information can include displaying, for one or more poses of the plurality of poses within the range of motion of the joint, a relationship between the pose and a distance between the first implant model and the second implant model. The distance can be a gap between the first implant model and the second implant model, an overlap of the first implant model and the second implant model, or both. Displaying can include displaying one or more points, one or more bar graphs, one or more pie charts, a measured quantity, a value, or any combination thereof.

In other examples, a user is enabled to change a pose of the first implant model, a pose of the second implant model, or both. Enabling can include enabling the user to change the pose of the first implant model, the pose of the second implant model, or both to preserve a distance between the first implant model and the second implant model through at least a portion of the range of motion of the joint. Preserving the distance can include maintaining the distance in a desired range. The desired range can be a range between 0 mm to 1.25 mm, inclusive. A user can be enabled to select a third implant model with a different size than the first implant model, wherein the third implant model is automatically associated with the representation of the first bone at a position of the first implant model.

In some examples, at least one point is mapped on a surface of the first implant model at a plurality of poses within the range of motion of the joint, inclusive, and at least one of the mapped points is aligned with the second implant model. A user can be enabled to change a pose of at least one of the first implant model and the second implant model to preserve a distance between the first implant model and the second implant model through at least a portion of the range of motion of the joint. A pose of at least one of the first implant model and the second implant model can be adjusted to achieve a desired relationship between the first implant model and the second implant model through at least a portion of the corrected range of motion of the joint.

In other examples, the computer is further configured to enable a user to change a pose of at least one of the first implant model and the second implant model to preserve a distance between the first implant model and the second implant model through at least a portion of the range of motion of the joint. Preserving the distance can include maintaining the distance in a desired range. The computer can be further configured to determine, based on the captured data, a relationship between the first implant model and the second implant model through at least a portion of the range of motion of the joint, and to generate a user interface that enables a user to select a pose at which the determined relationship is calculated, displayed, or both.

There can also be a computer program product, tangibly embodied in an information carrier, where the computer program product includes instructions being operable to cause a data processing apparatus to perform any of the methods described above.

Advantageously, implant positions can be planned using preoperative CT-derived models of a joint subject to a disease pathology by intraoperatively neutralizing defects caused by the disease pathology, applying a corrective force to align the bones of the limb to achieve a corrected pose (i.e., a desired limb alignment concurrent with appropriate ligament tension), capturing relative bone pose data with the limb in the corrected pose, and planning implant placement based on the captured bone pose data and preoperative CT-derived models. As a result, implant planning and bone cutting can be accomplished such that when the implants are installed, the postoperative result is a joint that can achieve the desired limb alignment with appropriate ligament tension throughout the range of motion of the joint.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

Figure 1A:
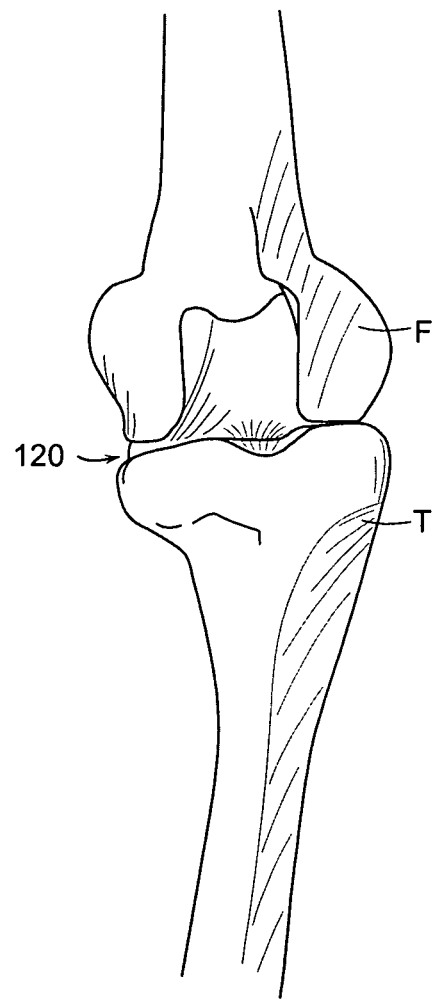
FIG. 1(a) is a front perspective view of a femur and a tibia of a knee joint at a pose with a flexion angle θ of 0 degrees.

Presently preferred embodiments are illustrated in the drawings. Although this specification refers primarily to unicondylar knee joint replacement surgery, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants. While some figures and associated descriptions refer primarily to medial unicompartmental knee arthroplasty (UKA), this is for description purposes only and is in no way intended to be limiting.

As used herein the term "pose" refers to position and/or orientation and includes, for example, defining three degrees of freedom (DOF) of position and/or three degrees of freedom of orientation (i.e., up to six DOF total) of an object. Pose can refer, for example, to a pose of a surgical tool (e.g., a position tracker, a cutting tool, etc.), a pose of a bone (e.g., a femur, a tibia), a pose of a joint (e.g., flexion angle, internal/external rotation, varus/valgus), a pose of a limb (e.g., a leg alignment), or a pose of any other object.

A system and method for implant planning using captured joint motion is described in U.S. patent application Ser. No. 11/963,547, filed Dec. 21, 2007, published as Pub. No. 2008/0262812 on Oct. 23, 2008, and incorporated by reference herein in its entirety. The method described below may be incorporated into the above-referenced implant planning method.

Bone pose (or joint motion) data collection can be used to aid in implant planning. Bone pose data shows the relative position of the bones of a joint (e.g., a femur and a tibia of a knee joint) and is preferably acquired based on the movement of a patient's actual physical joint (e.g., as the joint moves through a range of motion). Data can be acquired continuously as the joint moves through a range of motion (e.g., from flexion to extension) and/or at one or more discrete positions in the range of motion (e.g., at one or more specified flexion angles). For example, FIG. 1(a) shows a front view of a tibia T (e.g., a first bone) and a femur F (e.g., a second bone) of a knee joint 120 without any implant and with the joint 120 at full extension (i.e., a flexion angle $\theta$ of 0 degrees). To enable the pose (i.e., position and/or orientation) of each bone to be determined, position trackers (e.g., such as those shown in FIG. 15 and described in more detail below) that are detectable by a detection device, such as an optical camera, are affixed to the femur F and the tibia T of the joint 120. The detected poses of the tibia tracker and the femur tracker can be captured (e.g., recorded) at one or more specified joint flexion angles and/or in given degree intervals (e.g., 3 degrees) as the joint 120 is moved through a range of motion (e.g., from extension to flexion). Using transforms and registration techniques, as is well known, the detected pose of a tracker can be correlated to the pose of the physical bone on which the tracker is disposed. Additionally, the physical femur F and tibia T are registered, respectively, to numerical models of the femur F and the tibia T (e.g., to segmented CT data of the femur F and the tibia T acquired before the surgery begins and/or to representations or graphical models of the femur F and the tibia T generated, for example, from the segmented CT data). This registration establishes coordinate transformations between the femur F and the tibia T (i.e., the physical space) and the respective models of the femur F and the tibia T (i.e., the image space) so that the pose of the physical bones, which is determined from the detected poses of the position trackers, can be correlated to the models of the bones. Segmentation and registration may be accomplished using any known technique, such as the techniques described in U.S. Patent Publication 2006/0142657, published Jun. 29, 2006, which is hereby incorporated by reference herein in its entirety. Similarly, coordinate transformations may be determined using any known technique, such as the techniques described in U.S. patent application Ser. No. 11/750,840, filed May 18, 2007, published as Pub. No. 2008/0010705 on Jan. 10, 2008, which is hereby incorporated by reference herein in its entirety.

Figure 1B:
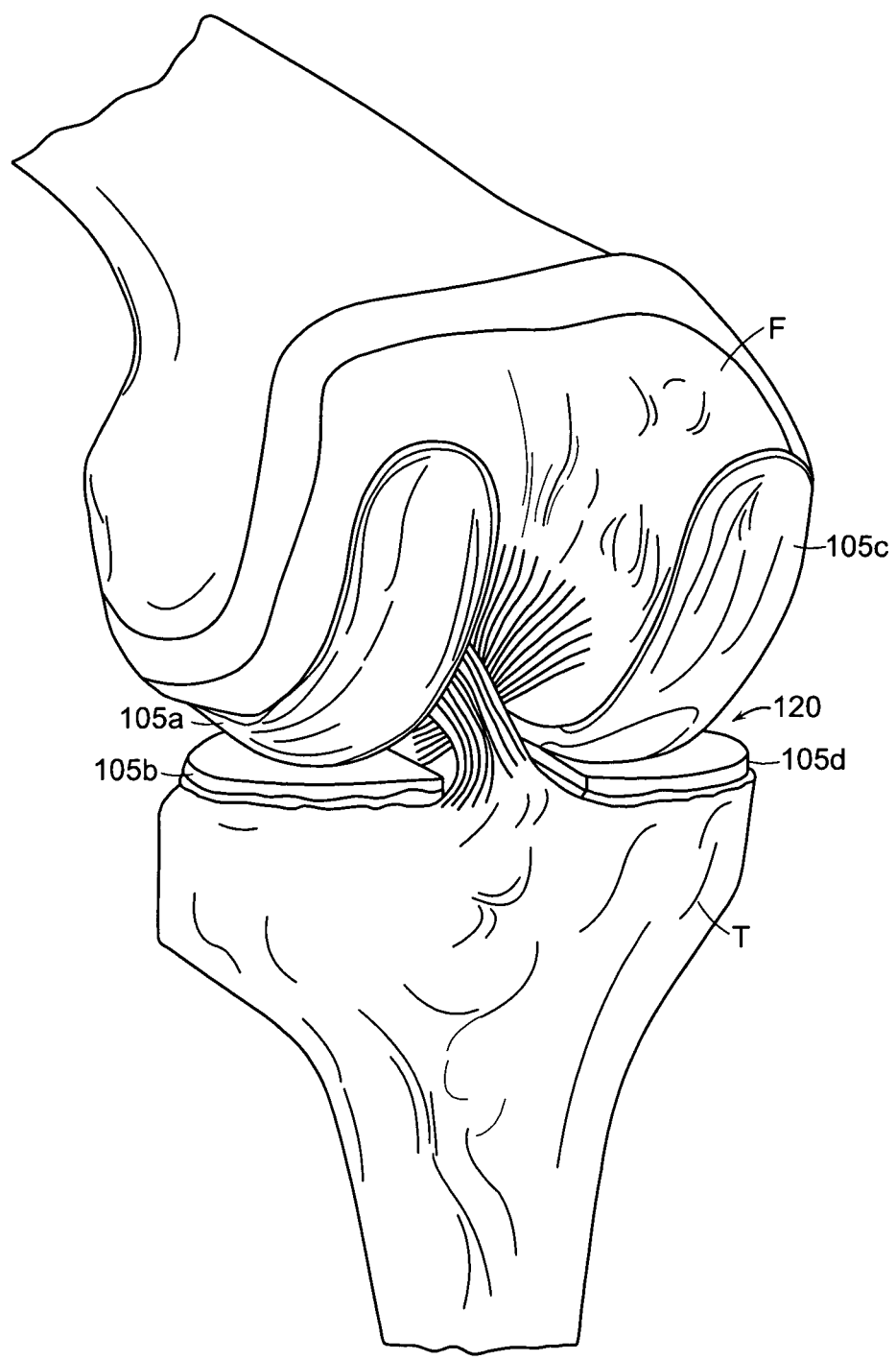
FIG. 1(b) is a perspective view of a conventional bicondylar knee arthroplasty system.

FIG. 1(b) shows a perspective view of the tibia T and the femur F of the knee joint 120 with a prosthetic device implanted in the joint 120. The prosthetic device includes a femoral component 105a and a tibial component 105b implanted in the medial compartment of the joint 120 and a femoral component 105c and a tibial component 105d implanted in the lateral compartment of the joint 120. In operation, the bearing surfaces of the femoral components 105a, 105c articulate with the bearing surfaces of the tibial components 105b, 105d as the joint 120 moves through a range of motion. The prosthetic device shown in FIG. 1(b) is a bicondylar implant because two compartments (e.g., medial and lateral) of the joint 120 are resurfaced by the prosthetic device. Alternatively, the prosthetic device could be a unicondylar implant that resurfaces only one compartment of the joint (e.g., medial or lateral) or a tricompartmental implant that resurfaces three compartments of the joint (e.g., medial, lateral, and patellofemoral), as described, for example, in U.S. patent application Ser. No. 11/684,514, filed Mar. 9, 2007, published as Pub. No. 2008/0058945 on Mar. 6, 2008, and hereby incorporated by reference herein in its entirety. The position of an implant component relative to the bone and other implant components impacts the postoperative performance of the joint 120. To determine where to place the implant components in the joint 120 to achieve desired joint kinematics, the surgeon can virtually plan implant placement prior to making any bone cuts. Implant planning may be accomplished, for example, as described in the above-referenced U.S. Patent Application Publication No. 2006/0142657. In some embodiments, the femur F and the tibia T of the knee joint 120 are virtually represented on a display screen, and the surgeon positions virtual models of the implant components relative to the images of the bones. The position of the virtual implant models can be manipulated and analyzed until the surgeon is satisfied with the virtual implant plan.

One goal of implant planning is to determine a placement of implant components that will restore healthy joint functionality, such as restoring a patient's limb to its natural pre-disease alignment, to a neutral alignment, and/or to a near neutral alignment for the particular patient. For example, when a normal, healthy knee joint is in a standing position, the femur and tibia may be neutrally aligned such that the hip center, knee center, and ankle center are in line, resulting in a neutral leg alignment (i.e., a neutral limb pose). As a result, when weight is born on the leg, both the medial and lateral femoral condyles articulate with the corresponding tibial articular surface. In contrast, when the knee joint is subject to a disease pathology, such as osteoarthritis, the joint may include defects such as osteophytes, capsular adhesions, osteochondral defects, and/or other defects that prevent the limb from achieving a healthy alignment.

Figure 1C:
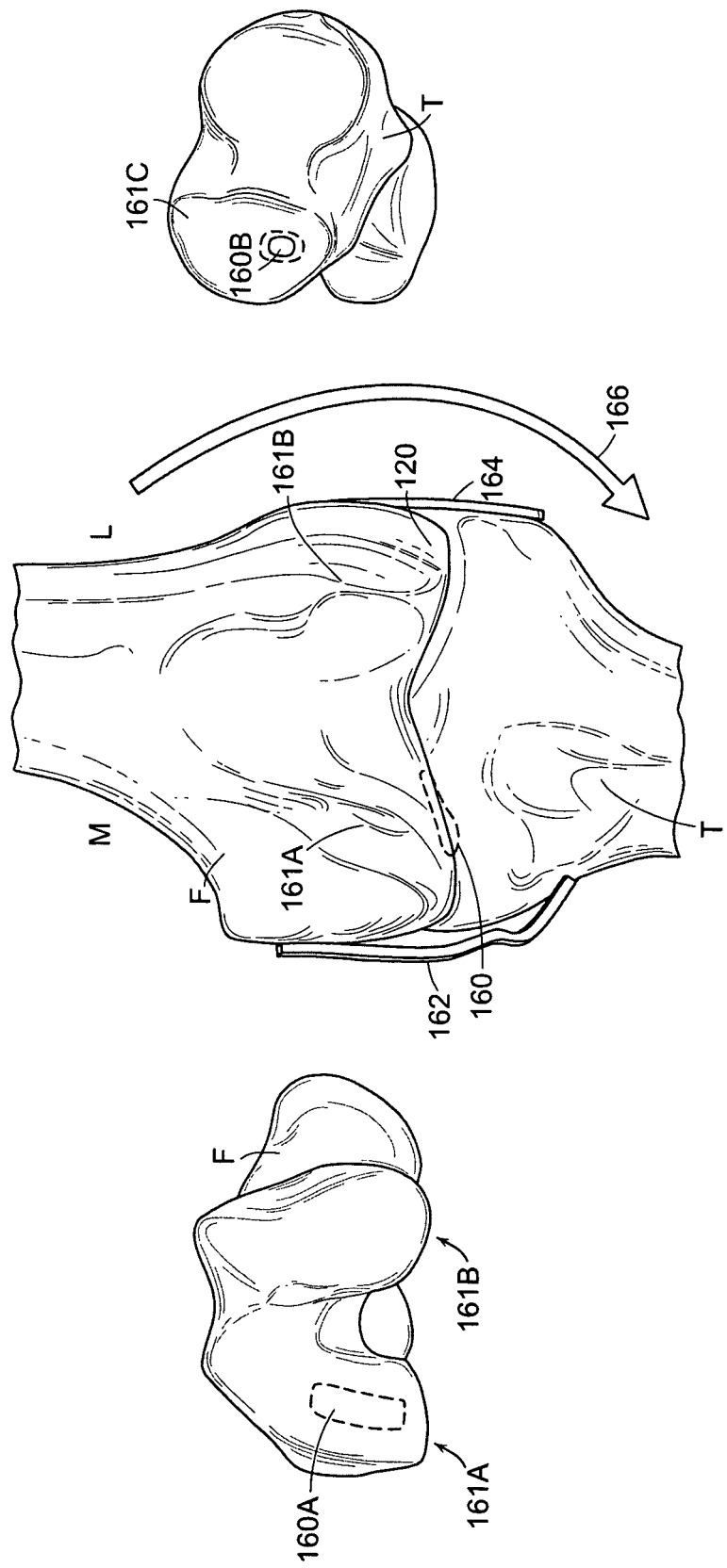
FIG. 1(c) is a front perspective view of a knee joint with a medial compartment defect associated with a disease pathology at a pose with a flexion angle θ of 0 degrees, in varus and with a varus moment applied.

FIG. 1(c) illustrates an example of a joint exhibiting a disease pathology. FIG. 1(c) shows a front view of the tibia T and the femur F (e.g., first and second bones) of the knee joint 120 at full extension, where the femur F includes a medial condyle 161A and a lateral condyle 161B, and the tibia T includes a corresponding tibial articular surface 161C. The joint 120 has a defect 160 associated with the disease pathology. In this example, the defect 160 occurs in the medial compartment of the joint 120 and includes a femoral deficit 160A and a tibial deficit 160B. The defect 160 can be, for example, a lack of material (e.g., cartilage and/or bone) in the medial joint space. Due to the missing material, when the joint 120 is loaded during stance, the defect 160 causes the medial compartment to collapse. As shown in FIG. 1(c), this results in a slack medial collateral ligament (MCL) 162, a varus moment 166 on the joint 120, and, under certain conditions, a taut lateral collateral ligament (LCL) 164. The varus moment 166 is a torque about the joint 120 that forces the limb into a varus pose. In a varus pose, the foot is disposed more medially than it would be in a neutral pose, a condition sometimes referred to as "bow-legged." Conversely, if the defect 160 is isolated to the lateral compartment of the joint 120, the lateral compartment would collapse under loading, resulting in a slack lateral collateral ligament (LCL) 164, a valgus moment on the joint 120, and, under certain conditions, a taut medial collateral ligament (MCL) 162. The valgus moment is a torque about the joint 120 that forces the limb into a valgus pose. In a valgus pose, the foot is disposed more laterally than it would be in a neutral pose, a condition sometimes referred to as "knock kneed." A patient having a disease pathology that is isolated to the medial compartment may be a candidate for medial unicondylar knee arthroplasty (UKA) using, for example, implants similar to the femoral component 105a and the tibial component 105b shown in FIG. 1(b). Similarly, a patient having a disease pathology that is isolated to the lateral compartment may be a candidate for lateral UKA using, for example, implants similar to the femoral component 105c and the tibial component 105d shown in FIG. 1(b).

One difficulty in determining how to place implant components in the joint 120 to correct poor joint kinematics caused by the disease pathology is that the disease pathology may prevent the limb from achieving an appropriate or desired pose (or alignment). The desired pose may be, for example, a neutral alignment, a near neutral alignment for the particular patient, and/or a natural pre-disease alignment. A disease pathology in the medial compartment of the joint, however, may limit the joint from being moved into a sufficiently less varus alignment. Similarly, a disease pathology in the lateral compartment of the joint may limit the joint from being moved into a sufficiently less valgus alignment. As a result, the preoperative images (e.g., CT scans) may only show the bones of the joint in the diseased, misaligned condition, which makes it difficult for the surgeon to accurately determine how to place the implant components in the joint to create a joint geometry that will enable the limb to postoperatively achieve the desired pose throughout the range of motion of the joint. The processes and apparatuses described herein advantageously enable the surgeon to capture bone pose data that shows how the patient's actual femur and tibia move relative to one another when aligned in the desired pose concurrently with appropriate ligament tension (the key for the restoration philosophy). The surgeon can then use the captured bone pose data to accurately select a position and orientation for each implant component (relative to the bone and other implant components) that will result in a joint geometry where the bones of the joint articulate as intended.

Figure 1D:
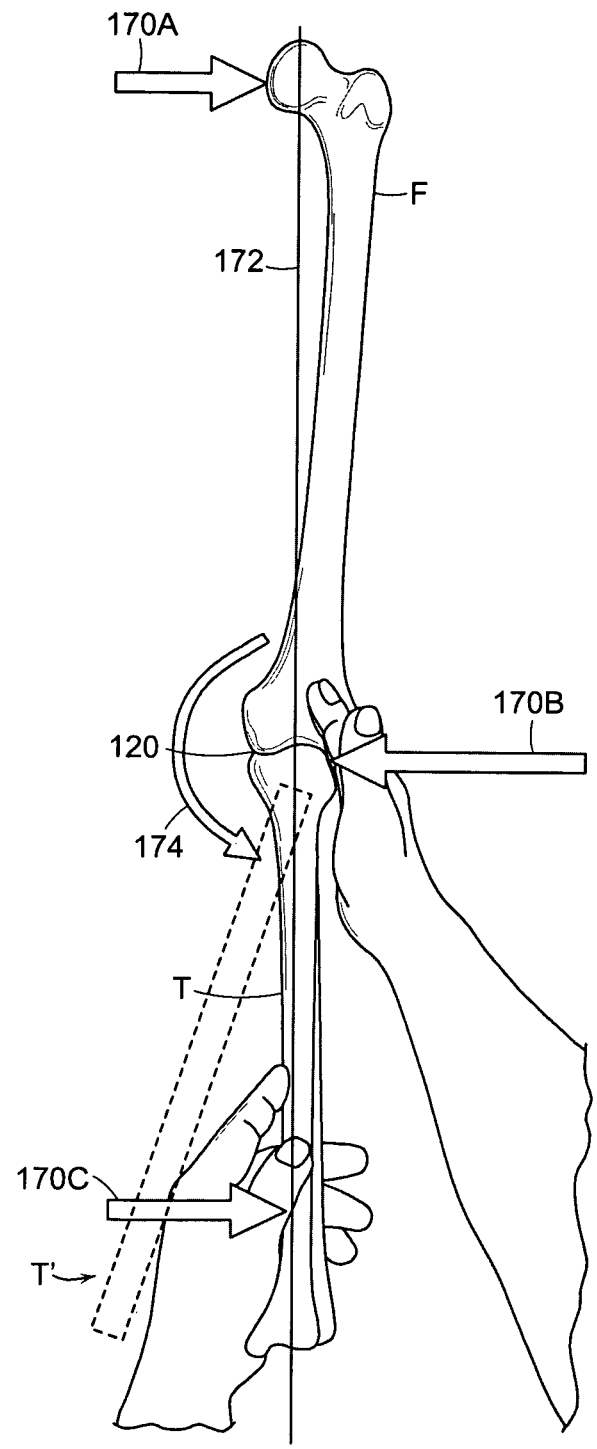
FIG. 1(d) is a perspective view of a knee joint with a medial compartment defect subject to a corrective force aligning the femur and tibia in a desired alignment.

According to an embodiment, FIG. 1(d) shows a perspective view of the knee joint 120 subject to a corrective force (170A, 170B, 170C, collectively 170). The corrective force is an applied force that simultaneously imparts appropriate ligament tension and aligns the femur F and the tibia T of the joint 120 such that the leg alignment is within a range of acceptable or appropriate alignment. The acceptable or appropriate alignment (also referred to as the desired alignment) may be any alignment appropriate to the patient's unique anatomy, such as a natural pre-disease state alignment, a neutral alignment, and/or an alignment that is near neutral for the particular patient. As discussed in detail below, when the applied corrective force 170 has a magnitude that is sufficient to impart the appropriate ligament tension, the resulting limb alignment should be within the acceptable range for the particular patient. In this embodiment, when the appropriate corrective force 170 is applied, the resulting alignment is a neutral alignment along the mechanical axis 172, which is a line passing through the hip center, knee center, and ankle center. To apply the corrective force 170, the surgeon can, for example, move the tibia T to induce a moment on the joint 120, as shown in FIG. 1(d) and explained in detail below. In this embodiment, the defect 160 is a medial defect resulting in the varus moment 166 (shown in FIG. 1(c)) that forces the leg into a varus pose (i.e., at a tibia T'). To counteract the varus moment 166, the surgeon can apply the corrective force 170 to induce a valgus moment 174 which acts to displace the ligament (i.e., the MCL 162) and move the leg from the varus alignment state (i.e., at the tibia T') to the desired alignment (i.e., at the tibia T along the mechanical axis 172). To impart appropriate ligament tension, the surgeon can increase the magnitude of the corrective force 170, for example, until the MCL 162 becomes taut (see, e.g., the MCL 162 in FIG. 1(f)). In some examples, moving the limb into the desired alignment is possible only after defects (e.g., osteophytes, capsular adhesions, etc.) in the joint have been addressed. As discussed below in connection with step 752 of FIG. 19, the surgeon can surgically neutralize such defects prior to applying the corrective force 170 to the limb. In a preferred embodiment, the defects are addressed intraoperatively just prior to application of the corrective force 170.

As noted above, the appropriate (or desired) alignment can be any alignment appropriate to the patient's unique anatomy. For example, the desired alignment can be based on the natural pre-disease state alignment, a neutral alignment, a near neutral alignment for the particular patient, the mechanical axis 172 of the leg, an anatomic axis of the femur F (not shown), an anatomic axis of the tibia T (not shown), the tension of one or more ligaments associated with the joint (e.g., the MCL 162, the LCL 164, etc.), and/or a desired clinical outcome. For some patients, a near neutral alignment that is slightly varus or slightly valgus may be more appropriate than a neutral alignment (e.g., based on geometric anatomical variations, such as hip width). The corrective force 170 corrects the tension of one or more ligaments associated with the joint, restoring the knee to an alignment uninfluenced by the effects of the disease pathology. The corrective force can be applied to one or more bones of the joint and/or the joint itself. For example, the corrective force can be applied to the femur F, the tibia T, and/or the joint 120.

Figure 1E:
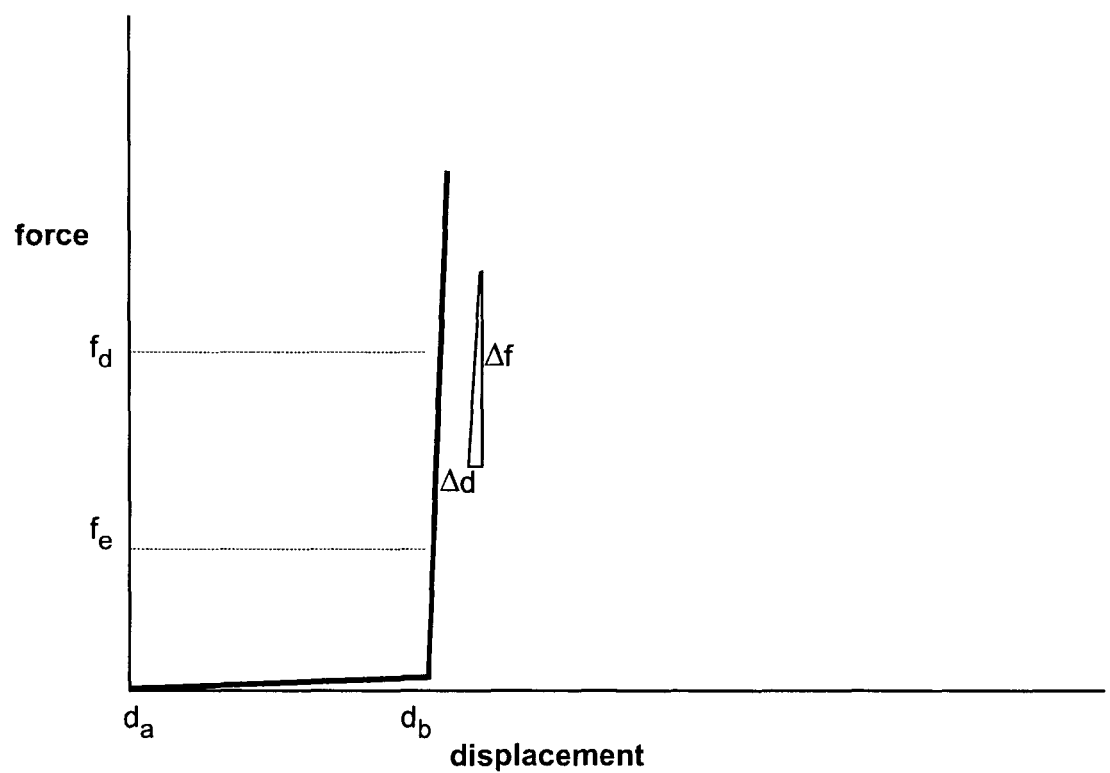
FIG. 1(e) is an exemplary graph of the corrective force applied to a joint and the resulting displacement of the ligament on the diseased side.

FIG. 1(e) is an exemplary graph, for a leg in a particular pose (e.g., the joint 120 at a specified flexion angle θ), of the force (i.e., vertical axis) of the MCL 162 in response to application of the corrective force 170 of FIG. 1(d) and the resulting displacement (i.e., horizontal axis) of the MCL 162 (or angulation of the joint 120) (e.g., the change from T' to T). Ligament tension (i.e., force) and pose variation (i.e., displacement) can be taken into consideration when determining the proper magnitude of the corrective force 170 for the particular pose. Depending on the magnitude of the corrective force 170, the corrective force 170 can induce displacement of the medial collateral ligament 162 (or angulation of the joint 120) from zero ($d_a$) to some larger value ($d_b$). Initially, the resistance force of the MCL 162 in response to application of the corrective force 170 would be low ($f_e$) because the MCL 162 is slack and thus offers little resistance. As long as the MCL 162 remains relatively slack, continued application of the corrective force 170 results in a significant change in displacement of the ligament (e.g., increases to $d_b$) while the magnitude of the corrective force 170 is only slightly increased (e.g., as shown in FIG. 1(e)). When the MCL 162 becomes taut, however, the resistance force of the MCL 162 builds, making it more difficult to displace. For example, as illustrated by the spike in the graph (e.g., at $d_b$), for the particular pose, the force of the MCL 162 increases a large amount for relatively small displacements. When the surgeon observes a minimal change of the ligament displacement for increased magnitudes of the corrective force 170, the MCL 162 is sufficiently taut. Thus, when the surgeon feels that the leg has generally stopped moving, the surgeon can stop increasing the magnitude of the corrective force 170. Maintaining the corrective force 170 at this magnitude will maintain the limb in an appropriate (or desired) alignment with appropriate ligament tension at that particular pose. In this example, if the surgeon imposes a valgus-induced moment resulting in either $f_e$ or $f_d$, the displacement is still approximately $d_b$. Continuing to increase the magnitude of the corrective force 170 provides no further benefit and could ultimately damage the ligament. Advantageously, due to the stiffness of the MCL 162, the magnitude of the corrective force 170 can vary and still result in the proper displacement to achieve the desired alignment. It should be noted that if the patient's ligament (e.g., the MCL 162) has been stretched such that the ligament will not become taut when the limb is in the range of acceptable alignment, the patient is likely not an appropriate candidate for unicondylar knee replacement and may require a different therapy, such as total knee replacement.

The appropriate magnitude of the corrective force 170 may be different at different leg poses (e.g., at different joint flexion angles). For example, a magnitude that works well at a first flexion angle θ (e.g., 40 degrees) may be excessive or insufficient at a second flexion angle θ (e.g., 90 degrees). Thus, when capturing corrected bone pose data, care should be taken to apply the appropriate degree of corrective force for each limb pose. For example, to aid in implant planning, bone pose data with the joint at a first flexion angle θ can be captured while a corrective force 170 having a first magnitude is applied to the leg to bring the leg into the desired alignment with appropriate ligament tension. The joint can then be moved to a second flexion angle θ and bone pose data can be captured while a corrective force 170 having a second magnitude is applied to the leg to bring the leg into the desired alignment with appropriate ligament tension. Bone pose data can also be captured continuously (e.g., in specified degree intervals) as the joint moves through a range of motion (e.g., from full extension to full flexion or any desired range). When continuous bone pose data is being collected, the corrective force 170 is continuously applied to maintain the appropriate ligament tension and alignment throughout the range of motion. The surgeon must take care, however, to vary the magnitude of the corrective force 170 as appropriate to ensure that the appropriate ligament tension and alignment are maintained at each limb pose throughout the range of motion. When the corrective force 170 is applied such that the limb simultaneously has appropriate ligament tension and appropriate alignment, the limb may be considered to be in a corrected pose or corrected alignment. Bone pose data taken with the limb in corrected poses throughout the range of motion of the joint represents a corrected range of motion of the joint.

For a lateral UKA compared to a medial UKA, the moments resulting from application of the corrective force are opposite, and the moment magnitude and "feel" experienced by the surgeon can be different. One reason the feel can be different is because the MCL 162 changes from slack to taut in a medial UKA, whereas the LCL 164 changes from slack to taut in a lateral UKA. Because the MCL 162 is stiffer than the LCL 164, the magnitude of corrective force required to achieve tautness will be different in both cases.

Figure 1F:
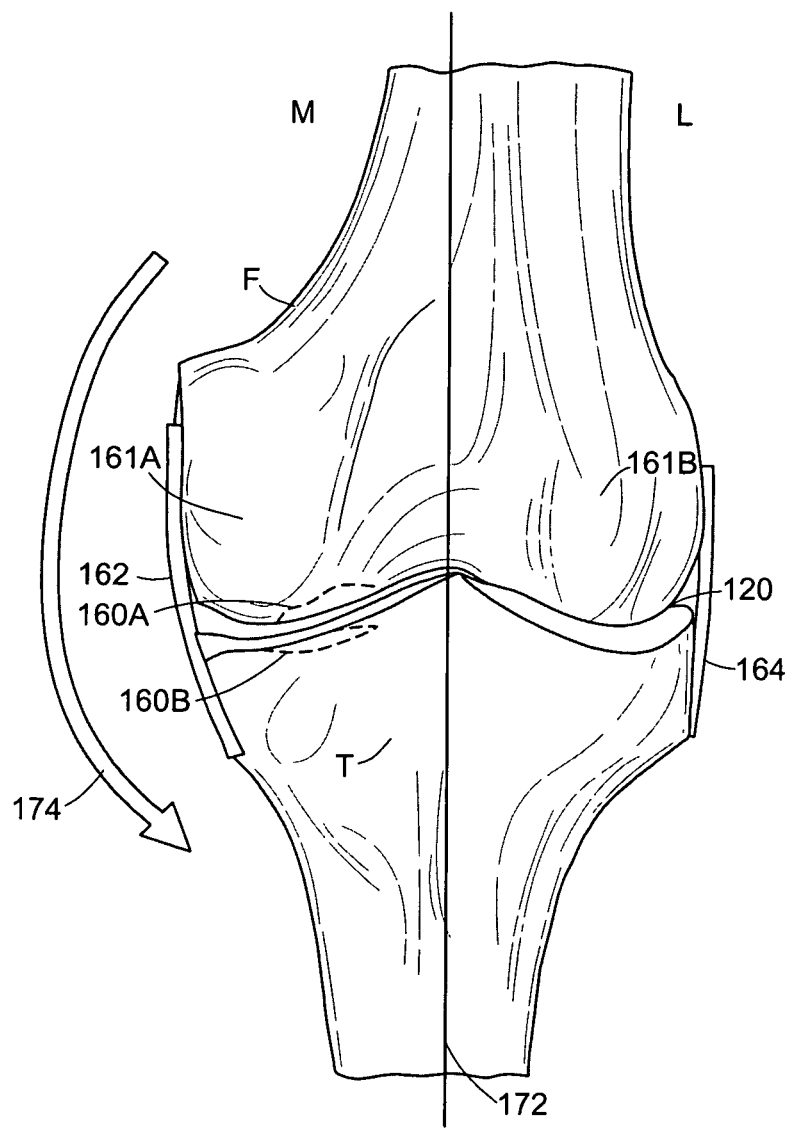
FIG. 1(f) is a detailed perspective view of the knee joint with a medial compartment defect of FIG. 1(c) subject to the corrective force as shown in FIG. 1(d) to align the femur and tibia in a desired alignment.

FIG. 1(f) is a detailed perspective view of the knee joint 120 with the medial compartment defect 160 of FIG. 1(c) subject to the corrective force 170 as shown in FIG. 1(d). If left uncorrected, the defect 160 creates a collapsed medial compartment, which can result in a slack MCL 162, a taut LCL 164, and an overall varus knee pose with a varus stress on the knee. As explained above, the corrective force 170 corrects the ligament tension and limb misalignment caused by the defect 160 by imparting the valgus moment 174 which acts to tension the MCL 162 and move the leg from the varus alignment state (i.e., FIG. 1(c)) to the desired alignment, which, in this embodiment, has the tibia T and the femur F aligned along the mechanical axis 172 of the leg. Advantageously, the femur F and the tibia T therefore achieve the desired corrected pose with appropriate ligament tension before any bone cuts are made, which facilitates implant planning. In particular, bone pose data with the limb in the corrected alignment can be captured (e.g., at one or more degrees of flexion) and used to plan placement of the implants in the joint 120 so the implants create a postoperative joint geometry where the femur F and the tibia T articulate as intended to achieve and maintain the desired alignment with appropriate ligament tension throughout the range of motion of the joint 120.

Figure 2:
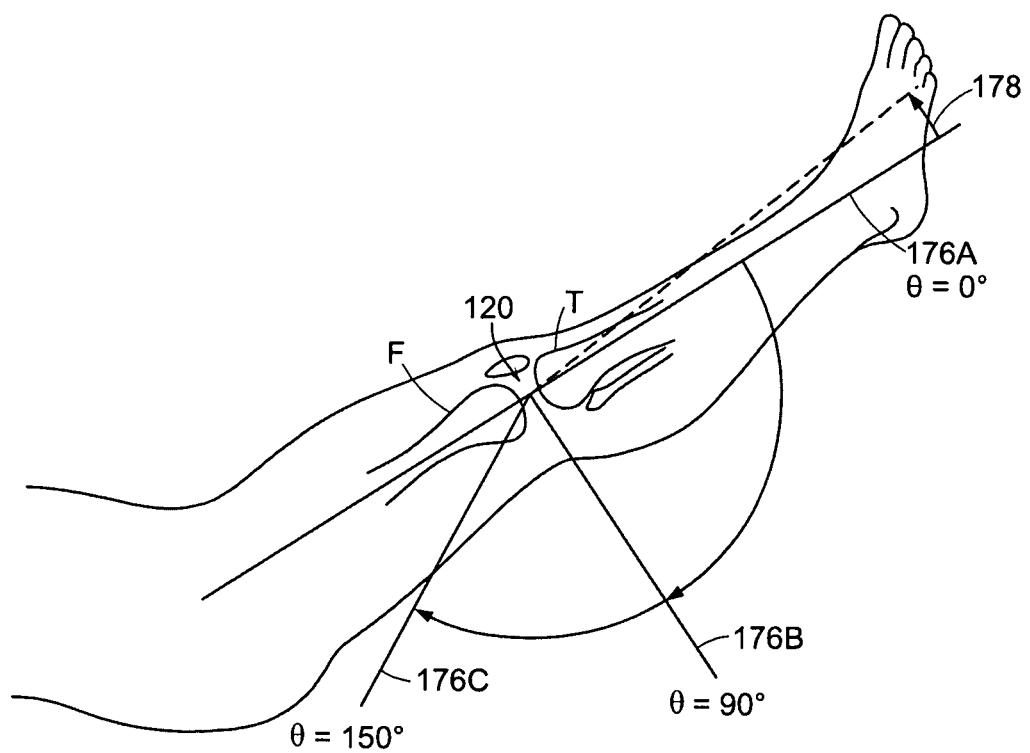
FIG. 2 illustrates a range of motion and poses at various flexion angles of a knee joint.

FIG. 2 illustrates a range of motion and limb poses at various flexion angles θ of the knee joint 120. The relative positions of the femur F and the tibia T change as the joint 120 moves through the range of motion resulting in a plurality of limb poses (e.g., pose 176A, 176B, and 176C, collectively poses 176) throughout the range of motion of the knee joint 120. The pose 176A results when the joint flexion angle θ=0° (e.g., full extension). The pose 176B results when the joint flexion angle θ=90°. The pose 176C results when the joint flexion angle θ=150° (e.g., full flexion). While only three poses 176 are shown, the limb can include any number of poses between, for example, joint flexion angles of θ=0° to θ>150°. Poses can also be captured with the joint 120 in extension 178 (e.g., beyond the flexion poses, i.e., hyperextension), between, for example, θ<0° to θ=−15° or less.

Although not illustrated in FIG. 2, joint motion can occur in six degrees of freedom. A knee joint can exhibit the angular range of motion between full extension and full flexion with some concurrent internal and/or external rotation. Throughout this motion, the relationship between the femur and the tibia changes (e.g., changing areas of contact). The relationship of the bones to the soft tissue (e.g., medial and lateral collateral ligaments (MCL/LCL), anterior and posterior cruciate ligaments (ACL/PCL), etc.) also changes. For example, considering the femur F as fixed and the tibia T moving relative to the femur F, the motion of the joint 120 can include the patient's entire range of flexion and/or extension (between extremes of about θ=−15° to θ=150°, e.g., as shown in FIG. 2 and hereafter referred to as the specific patient's flexion/extension range of motion (F/E ROM)), the patient's internal and/or external rotation of the tibia T, and/or abduction and/or adduction (e.g., varus and/or valgus). The joint 120 can include translations, such as medial and/or lateral translation, anterior and/or posterior translation, and/or distal and/or proximal translation. The exact ranges and displacements are patient-specific and the "natural" ranges and translations also depend on the nature and magnitude of imposed external forces.

Figure 3:
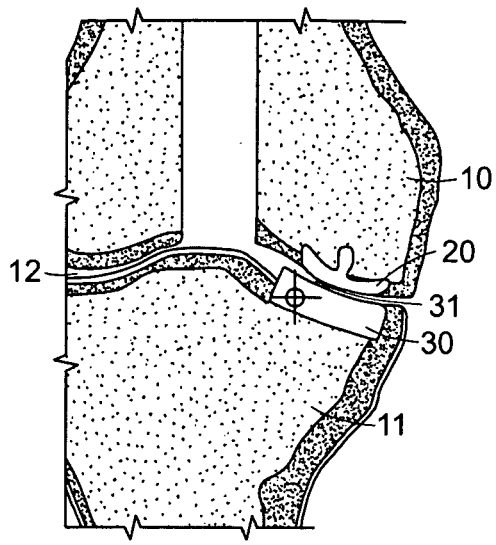
FIG. 3 is a front cross sectional view of an embodiment of a representation of a joint at a pose with a flexion angle θ of 0 degrees.
Figure 4:
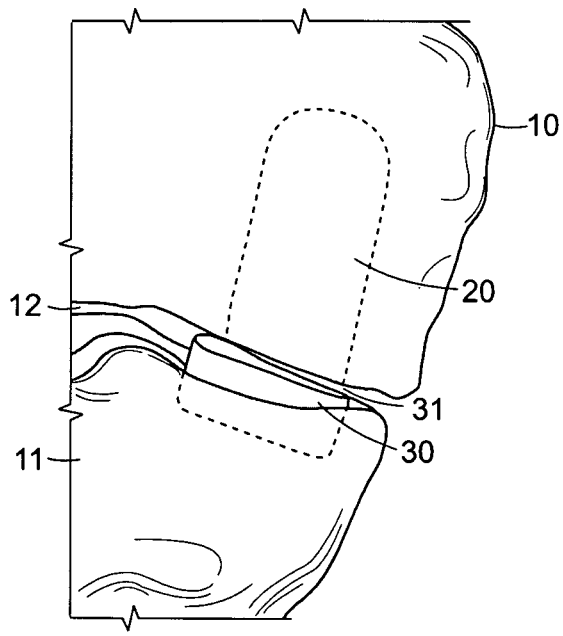
FIG. 4 is a front perspective view of the representation of FIG. 3.

FIG. 3 shows a cross sectional view of a 2D display of a virtual representation 12 of the joint 120 at a flexion angle θ of 0 degrees. Similarly, FIG. 4 shows a 3D display of the virtual representation 12 of the joint 120 at a flexion angle θ of 0 degrees. As shown in FIG. 3, the virtual representation 12 of the joint 120 can include a representation 10 of the femur F and a representation 11 of the tibia T. A tibial implant model 30 (e.g., a first implant model) and a femoral implant model 20 (e.g., a second implant model) can be associated with (e.g., registered to) the representation 11 of the tibia T and the representation 10 of the femur F, respectively, so that the implant models 20, 30 are in the same coordinate system as the representations 10, 11. This may be accomplished in any known manner, such as, for example, the implant planning process described in the above-referenced U.S. Patent Application Publication No. 2006/0142657. In some embodiments, the representations 10, 11 are graphic models of the femur F and the tibia T generated from segmented CT data as is well known. To directly compare the relationship between two implant models at any desired flexion angle θ let $T_{ifd}$ be the transform from the femoral implant model 20 to the femoral CT data and $T_{itd}$ be the transform from the tibial implant model 30 to the tibial CT data. Then the femoral implant model 20 can be positioned relative to the tibial implant model 30 at any desired flexion angle θ by using the relationship $T_{ifd} T_{fd}^{-1} T_{tf}^{-1} T_{td} T_{itd}^{-1}$.

This registration enables the captured bone pose data taken throughout the range of motion of the joint 120 to be "played back" to the user so the user can visualize the relative motion of the femur F and tibia T of the CT data with the femoral and tibial implant models 20, superimposed on the representations 10, 11 of the femur F and the tibia T of the joint 120. For example, based on the captured bone pose data, the physical motion of the joint 120 can be visualized by displaying the representation 10 of the femur F and the representation 11 of the tibia T and moving the representations 10, 11 in accordance with how the femur F and the tibia T actually move. If the bone pose data was captured while the appropriate corrective force 170 was applied to the leg, the "play back" represents the relative positions of the femur F and the tibia T when the limb in is the desired alignment with appropriate ligament tension. The surgeon can then position the implant models 20, 30 to substantially maintain the corrected joint geometry throughout the range of motion so that the limb will achieve the appropriate ligament tension and desired alignment when the corresponding physical implant components are installed in the joint. For example, when the implant models 20, 30 are superimposed on the representations 10, 11 (e.g., as shown in FIG. 3), the relative position of the implant models 20, can be seen at any selected pose (e.g., flexion angle θ) within the range of motion of the joint 120. The user can also determine whether there is a gap (i.e., a space) or an overlap (i.e., an interference) between the implant models 20, 30 at any selected pose within the range of motion of the joint 120. Gap and overlap are discussed further below in connection with FIGS. 5 and 9.

Figure 6:
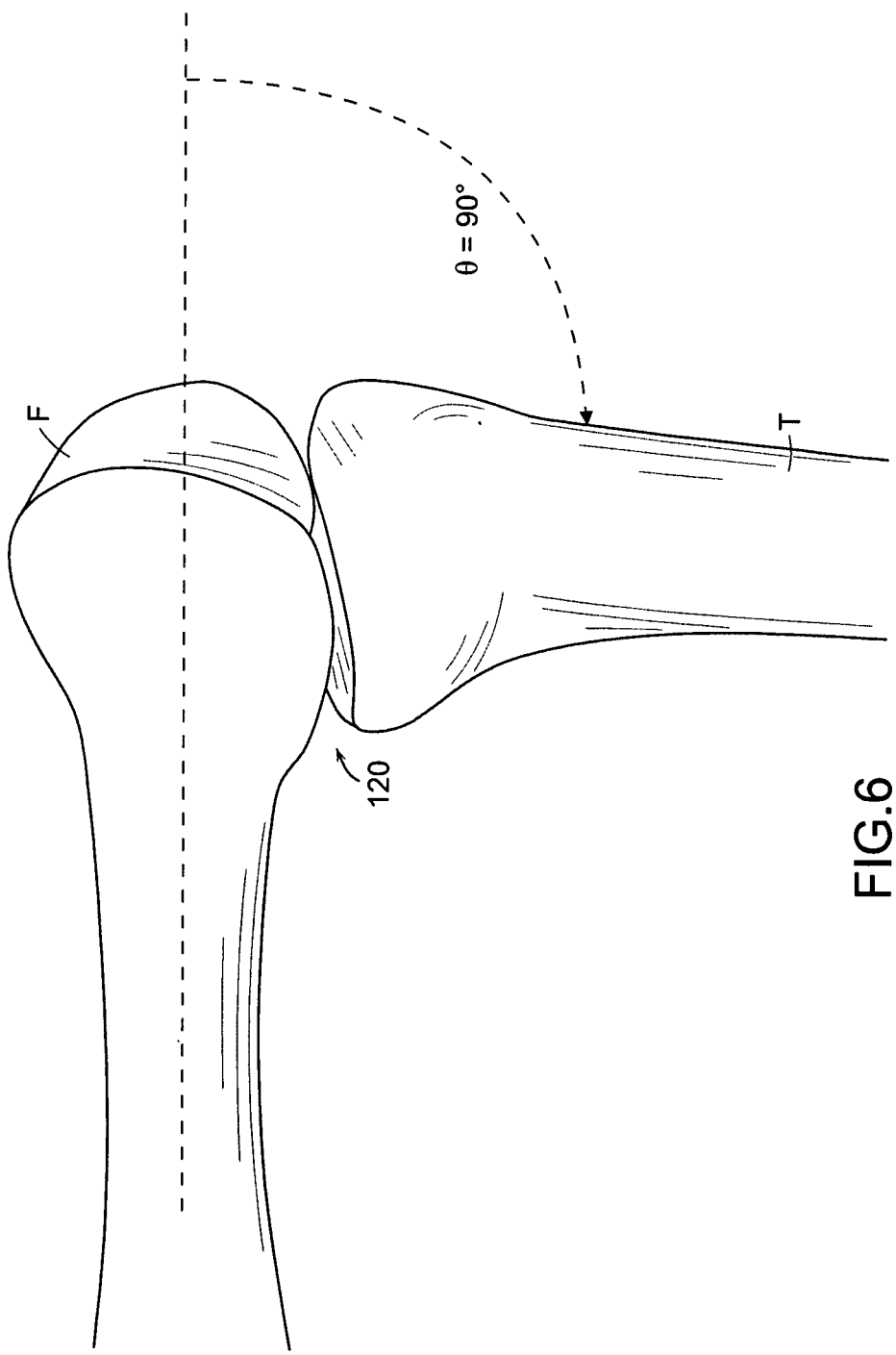
FIG. 6 is a side view of the femur and the tibia of FIG. 1 at a pose with a flexion angle θ of 90 degrees.
Figure 7:
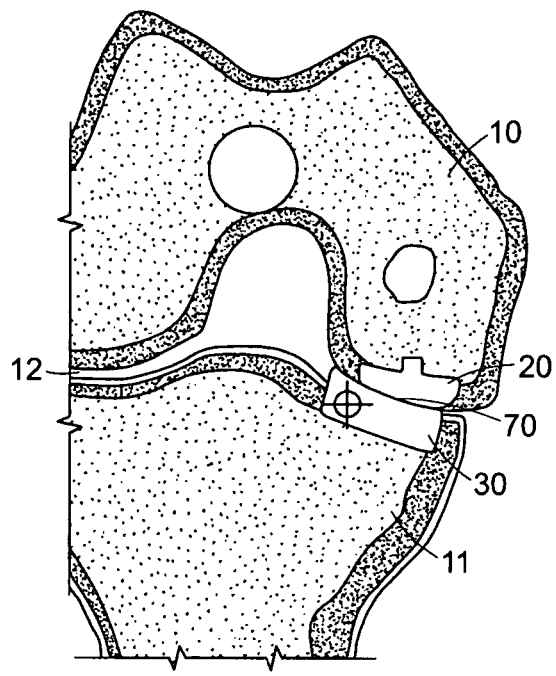
FIG. 7 is a front cross sectional view of an embodiment of a representation of a joint at a pose with a flexion angle θ of 90 degrees.
Figure 8:
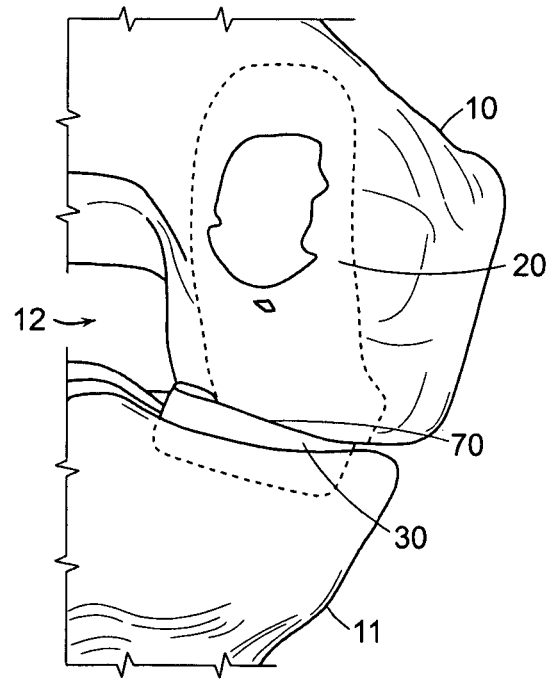
FIG. 8 is a front perspective view of the representation of FIG. 7.

Anatomical axes can be defined in the CT data for the femur F and the tibia T of the joint 120. Once this has been done, anatomical angles (e.g., flexion angle θ, varus/valgus angle, internal/external angle) for any pose of the joint 120 can be computed and displayed for any position and/or orientation of the captured data or in "real time" as the joint 120 is manipulated. FIG. 6 shows a side view of the femur F and the tibia T of the joint 120 without any implant where the joint 120 has a flexion angle θ of 90 degrees. The amount of gap or overlap between the implant models 20, 30 can be determined for the implant models 20, 30 associated with (e.g., superimposed on) the representations 10, 11 of the femur F and the tibia T at a selected pose with flexion angle θ (e.g., 0 degrees as shown in FIG. 3, 90 degrees as shown in FIG. 6) of the joint 120. This information can be used to plan the placement in the joint 120 of the actual implants that correspond to the implant models 20, 30. For example, if an overlap 70 is detected between the implant models 20, 30 (as shown in FIGS. 7 and 8), the surgeon may decide to reposition the femoral implant model 20 and/or the tibial implant model 30 to eliminate the overlap 70.

According to some embodiments, one or more implant models may be used. For example, as described above, in some embodiments, both the femoral implant model 20 and the tibial implant model 30 may be used to evaluate relative positions of the two implant models 20, 30. This embodiment may be useful in cases where a patient is having both the femur F and the tibia T resurfaced. In such cases, the implant models 20, 30 can be used to plan placement of the actual femoral and tibial implant components that will be implanted in the femur F and the tibia T of the patient. Alternatively, in another embodiment, only the tibial implant model 30 may be used to evaluate relative positions between the tibial implant model 30 and a surface of the representation 10 of the femur F. The surface of the representation 10 may correspond, for example, to an actual surface of the patient's femur F or to a previously installed implant that is now part of the patient's joint 120. This embodiment may be useful in cases where the femur F is not being resurfaced at all or where a previously installed femoral implant is not being replaced or modified. Similarly, in another embodiment, only the femoral implant model 20 may be used to evaluate relative positions of the femoral implant model 20 and a surface of the representation 11 of the tibia T. The surface of the representation 11 may correspond, for example, to an actual surface of the patient's tibia T or to a previously installed implant that is now part of the patient's joint 120. In other embodiments, additional implant models may be included, such as models of independent segmented components described in U.S. patent application Ser. No. 11/684,514, filed Mar. 9, 2007, published as Pub. No. 2008/0058945 on Mar. 6, 2008, and hereby incorporated by reference herein in its entirety.

As described above, the placement of one implant model relative to another or the placement of an implant model relative to a surface of a bone or a previously installed implant can be visualized and analyzed throughout the range of motion of the joint 120. For example, the relative placement of the tibial implant model 30 and the femoral implant model 20 can be visualized and evaluated. In some embodiments, when the lowest signed distance between the surface of the femoral implant model 20 and the surface of the tibial implant model 30 is a positive value, a gap 31 is detected between the implant models 20, 30 as shown in FIGS. 3 and 4.

Figure 5:
FIG. 5 illustrates an embodiment of a computer display of a gap analysis at a pose with a flexion angle θ of 0 degrees.

FIG. 5 shows an example computer display of a gap analysis of the positions of the implant models 20, 30. In some embodiments, the computer display includes a user input 50 for inputting a selected flexion angle θ for a pose and an indicator 51 that shows a value of the gap 31 at the selected flexion angle θ. In the example of FIG. 5, at a pose with a flexion angle θ of 0 degrees, there is a gap 31 of 1.2 mm between the femoral implant model 20 and the tibial implant model 30. Likewise, when the lowest signed distance between the surfaces of the implant models 20, 30 is a negative value, an overlap is detected between the implant models 20, 30.

FIG. 7 shows a front cross sectional view of a 2D display of the representations 10, 11 of the femur F and the tibia T. Also shown in FIG. 7 are the implant models 20, 30 associated with the representations 10, 11 of the femur F and the tibia T at a pose with a flexion angle θ of 90 degrees.

FIG. 8 shows a front view of a 3D display of the representations 10, 11 of the femur F and the tibia T associated with the representations of the femoral implant model 20 and the tibial implant model 30 at a pose with a flexion angle θ of 90 degrees.

Figure 9:
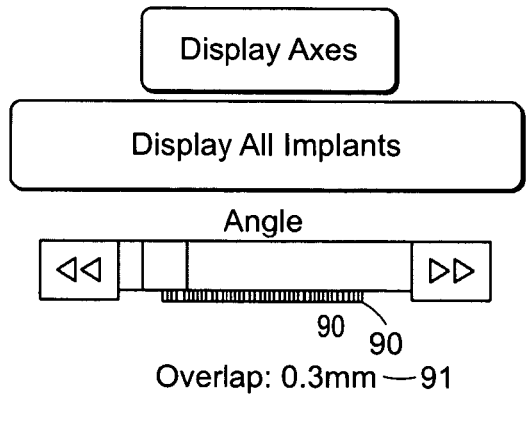
FIG. 9 illustrates an embodiment of a computer display of an overlap analysis at a pose with a flexion angle θ of 90 degrees.

FIG. 9 shows an example of a computer display of an overlap analysis of the positions of the implant models 20, 30 at a pose with a flexion angle θ of 90 degrees. In some embodiments, the computer display includes a user input 90 for inputting a selected flexion angle θ and an indicator 91 that shows a value of the overlap 70 at the selected flexion angle θ. In the example of FIG. 9, at a pose with a flexion angle θ of 90 degrees, there is an overlap of 0.3 mm between the femoral implant model 20 and the tibial implant model 30. Based on the information provided by the virtual analysis shown in FIGS. 5 and 9, when a surgeon is planning the placement of actual implants corresponding to the implant models 20, 30, he can adjust the implant models 20, 30 to achieve the desired relationship between the implant models 20, 30 at any selected pose (e.g., angle θ) within the range of motion of the joint. For example, the surgeon may adjust the implant models 20, 30 to ensure that the gap 31 is filled at the pose with a flexion angle θ of 0 degrees and the overlap 70 is removed at the pose with a flexion angle θ of 90 degrees by repositioning the implant models 20, 30 until the surfaces of the implant models 20, 30 just "touch" each other at selected pose angles within the range of motion of the joint 120.

Figure 9A:
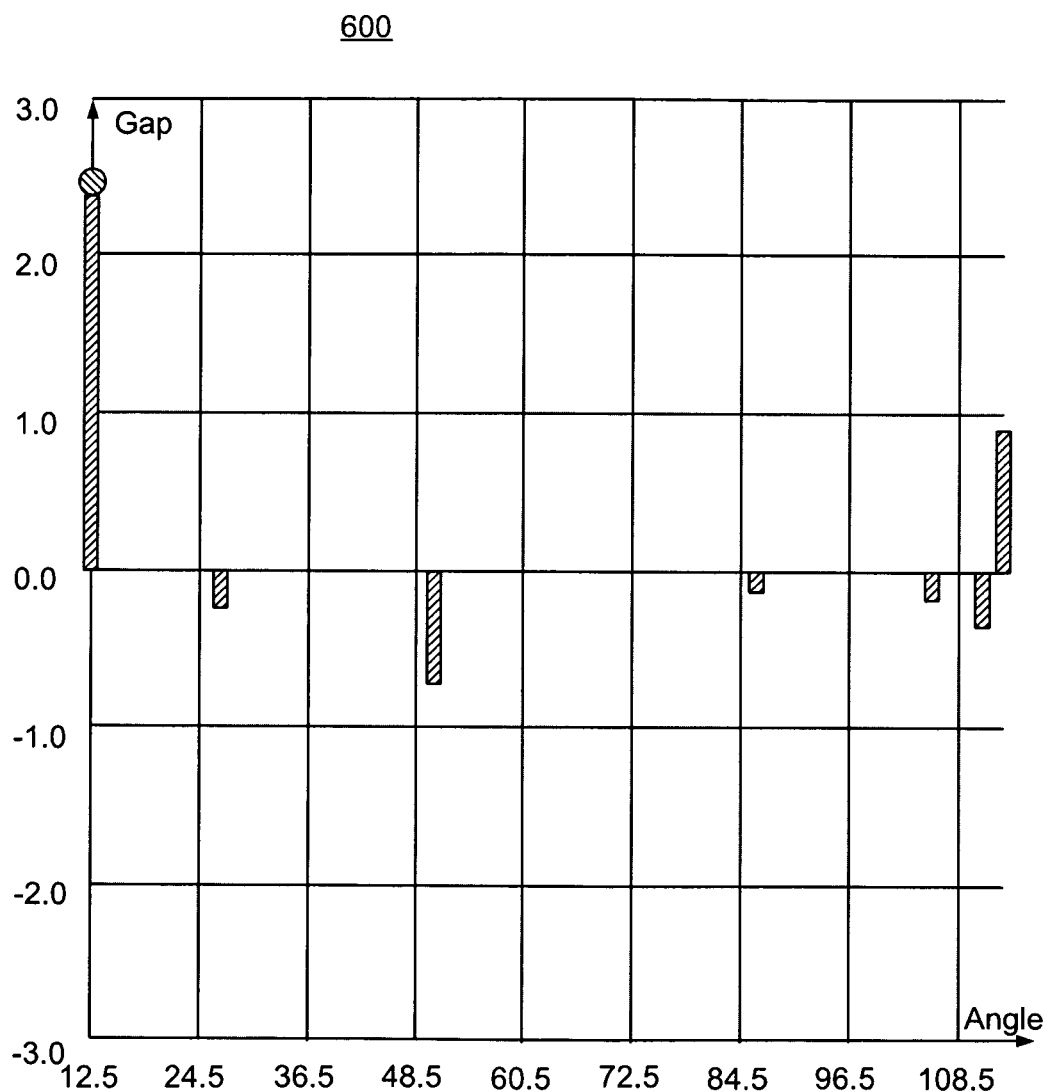
FIG. 9(a) illustrates an embodiment of a computer display of a graph of the gap/overlap analysis over a range of flexion angles.

FIG. 9(a) shows another example of a computer display with a graph 600 that graphs the gap/overlap analysis of the positions of the implant models 20, 30 over a range of flexion angles. The horizontal axis of the graph 600 displays the value of the flexion angle θ of a corresponding pose. Although the exemplary graph 600 includes angles 12.5 degrees through 108.5 degrees, any range of angles can be displayed. The vertical axis of the graph 600 displays the value of the calculated gap or overlap between two measured points (e.g., the first implant model and the second bone, the first implant model and the second implant model, etc.). In the graph 600, the positive values on the ordinate represent a gap between the two measured points, with the number representing the distance of the gap, in millimeters. In the graph 600, the negative values on the ordinate represent an overlap between the two measured points, with the number representing the distance of the overlap, in millimeters. As described herein, the position of the implant(s) can be manipulated through the user interface so the surgeon can see the gap/overlap analysis for different implant positions. In such situations, the graph 600 updates as the implant positions are adjusted. With the graph, the user (e.g., the surgeon) can advantageously see all gaps and overlaps over the entire angular range of motion in one display. This enables the user to slightly modify the position of the implant(s) and receive feedback on the modification over the entire angular range. The user can then adjust the position to achieve a desired goal (e.g., minimize all gaps and overlaps, minimize center gaps and overlaps at the expense of larger gaps and overlaps at the ends of the range, etc.).

The movement of the femur F and tibia T of the joint 120 can be captured and registered both before and after bone cutting and can be used to compare preoperative and intraoperative ranges of motion of the joint 120 to determine if any over-correction or under-correction has occurred. Accordingly, the surgeon can adjust the implant plan and continue to cut the bone to adjust as desired.

Figure 11:
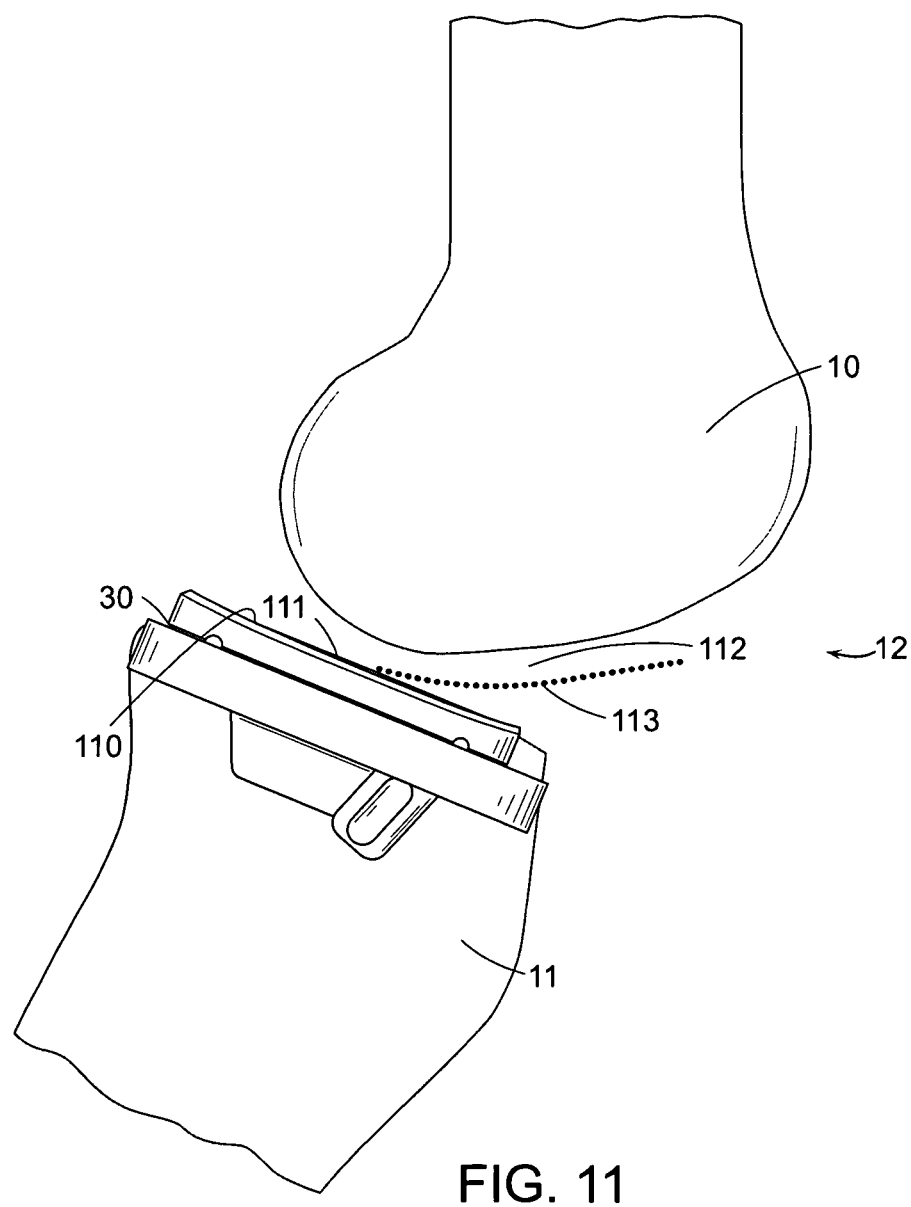
FIG. 11 is a side view of the representation of FIG. 10 at a pose with a second flexion angle θ and showing an embodiment of a point mapping of a first implant model.
Figure 12:
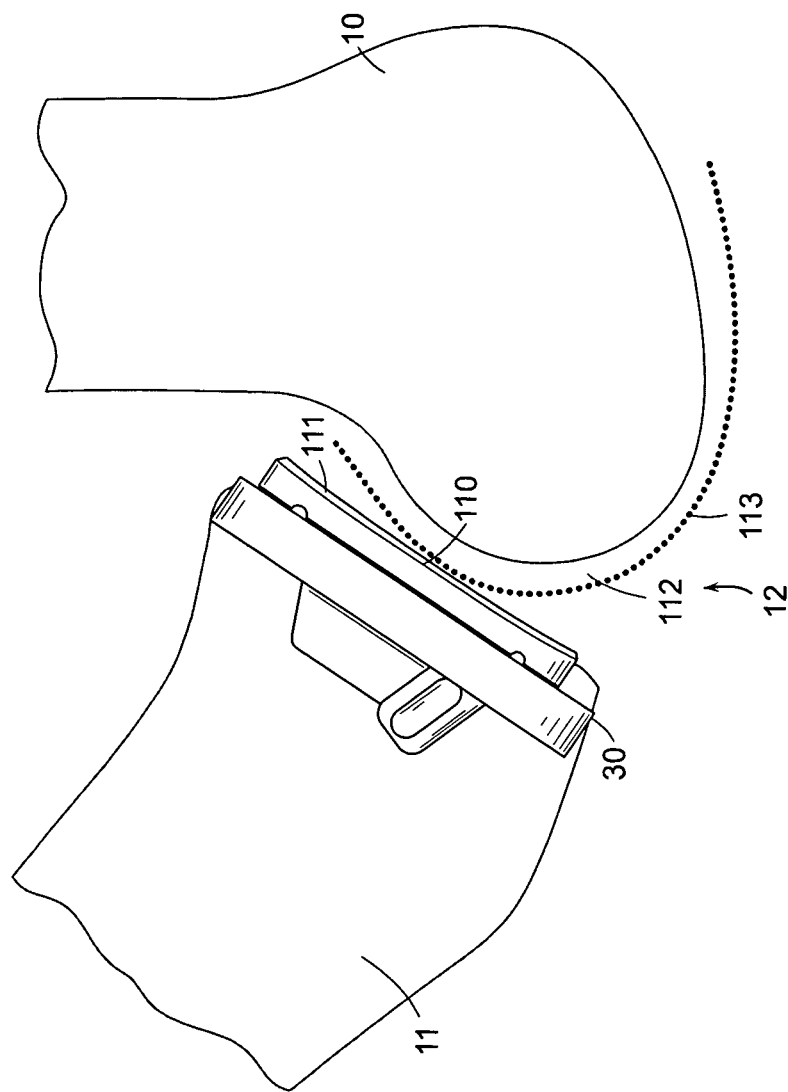
FIG. 12 is a side view of the representation of FIG. 10 at a pose with a third flexion angle θ and showing an embodiment of a point mapping of a first implant model.
Figure 13:
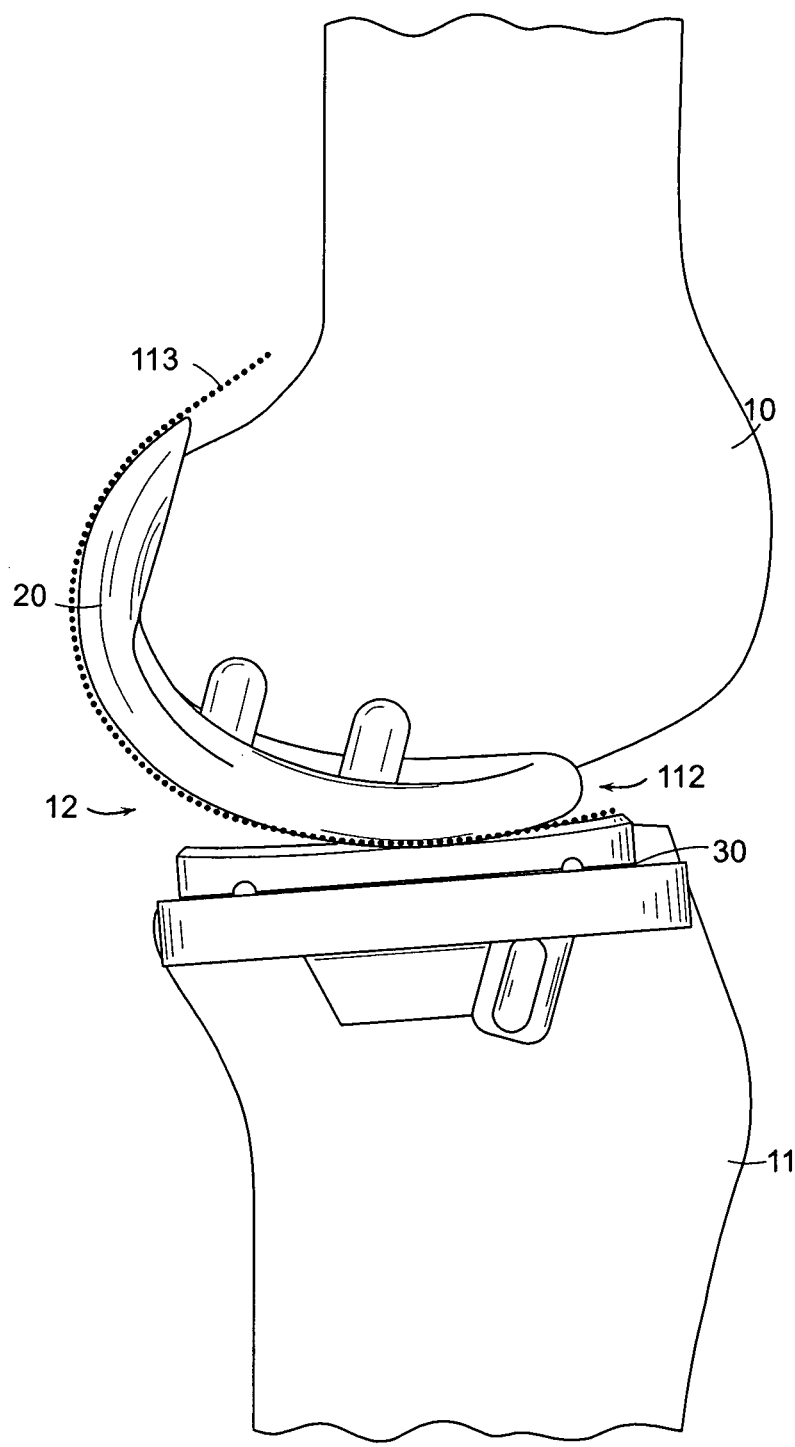
FIG. 13 is a side view of the representation of FIG. 10 showing an embodiment of a point mapping of a first implant model and a second implant model positioned relative to the point mapping.

Referring to FIGS. 11-13, further analysis can be performed by selecting one or more points on the articulating surface of a first implant model (e.g., points near the center, anterior, and posterior of the surface of the tibial implant model 30), mapping these points at multiple poses of joint flexion into the space of an opposite bone (e.g., the representation 10 of the femur F) and/or a second counterpart implant model (e.g., the femoral implant model 20) using the transform relationships described previously, and displaying these mapped points in 3D or projected 2D relative to the opposite bone and/or the second implant model. Mapping may be accomplished, for example, by determining a position of each of the selected points at each of the multiple poses of joint flexion. These "mapped" points can then be used to guide the placement of the second implant model. For example, the second implant model (e.g., the femoral implant model 20) can be positioned so that the articulating surface of the second implant model has a desired relationship to the articulating surface of the first implant model (e.g., the tibial implant model 30) as represented by the mapped points. Similarly, the first implant model (e.g., the tibial implant model 30) can be positioned so that the articulating surface of the first implant model will have a desired relationship to the articulating surface of the opposite bone (e.g., the representation 10 of the femur F). Repositioning the first implant model will update the positions of the mapped points so that the relationship of the second implant model and/or the opposite bone to the first implant model can always be reestablished.

One example of this is to select central, anterior, and posterior points on the surface of a tibial implant model and use these mapped points to align the position and/or orientation of a femoral implant model as illustrated in FIGS. 11-13.

Figure 10:
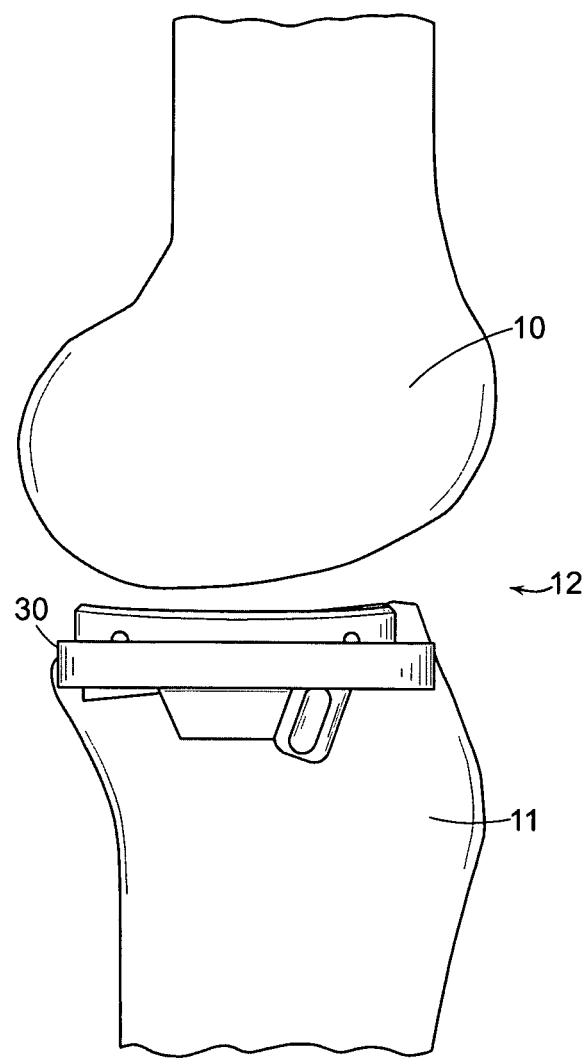
FIG. 10 is a side view of an embodiment of a representation of a joint at a pose with a first flexion angle θ.

For example, FIG. 10 shows a side view of a representation 12 of the joint 120. The representation 12 includes the representations 10, 11 of the femur F and the tibia T, respectively, for the joint 120 at a flexion angle θ of 0 degrees. A first implant model 30 is associated with (e.g., superimposed on or registered to) the representation 11 of the tibia T. The representations 10, 11 can be used to accomplish point mapping. According to some embodiments, as shown in FIGS. 11 and 12, one or more points 110 of an articulating surface 111 of the first implant model 30 can be mapped to an articular space 112 of the femur F at multiple poses of the range of motion of the joint 120. The mapped points 113 are preferably displayed relative to the representations 10, 11. FIG. 11 shows the mapped points 113 with the representation 12 of the joint 120 at a pose with a flexion angle θ of approximately 30 degrees. FIG. 12 shows the mapped points 113 with the representation 12 of the joint 120 at a pose with a flexion angle θ of approximately 135 degrees.

FIG. 13 shows the representations 10, 11 of FIG. 11, the first implant model 30 that has been associated with the representation 11, and a second implant model 20 that has been associated with the representation 10. In some embodiments, the second implant model 20 may be associated with the representation 10 by aligning the articular surface of the second implant model 20 with at least one of the mapped points 113 as shown in FIG. 13. In this manner, a desired relationship between the implant models 20, 30 may be achieved. As a result, the physical implant components (which correspond to the implant models 20, 30) will have the desired relative placement through some or all of the range of motion of the joint 120 when implanted in the patient's joint 120 by the surgeon in accordance with the implant plan.

Figure 14:
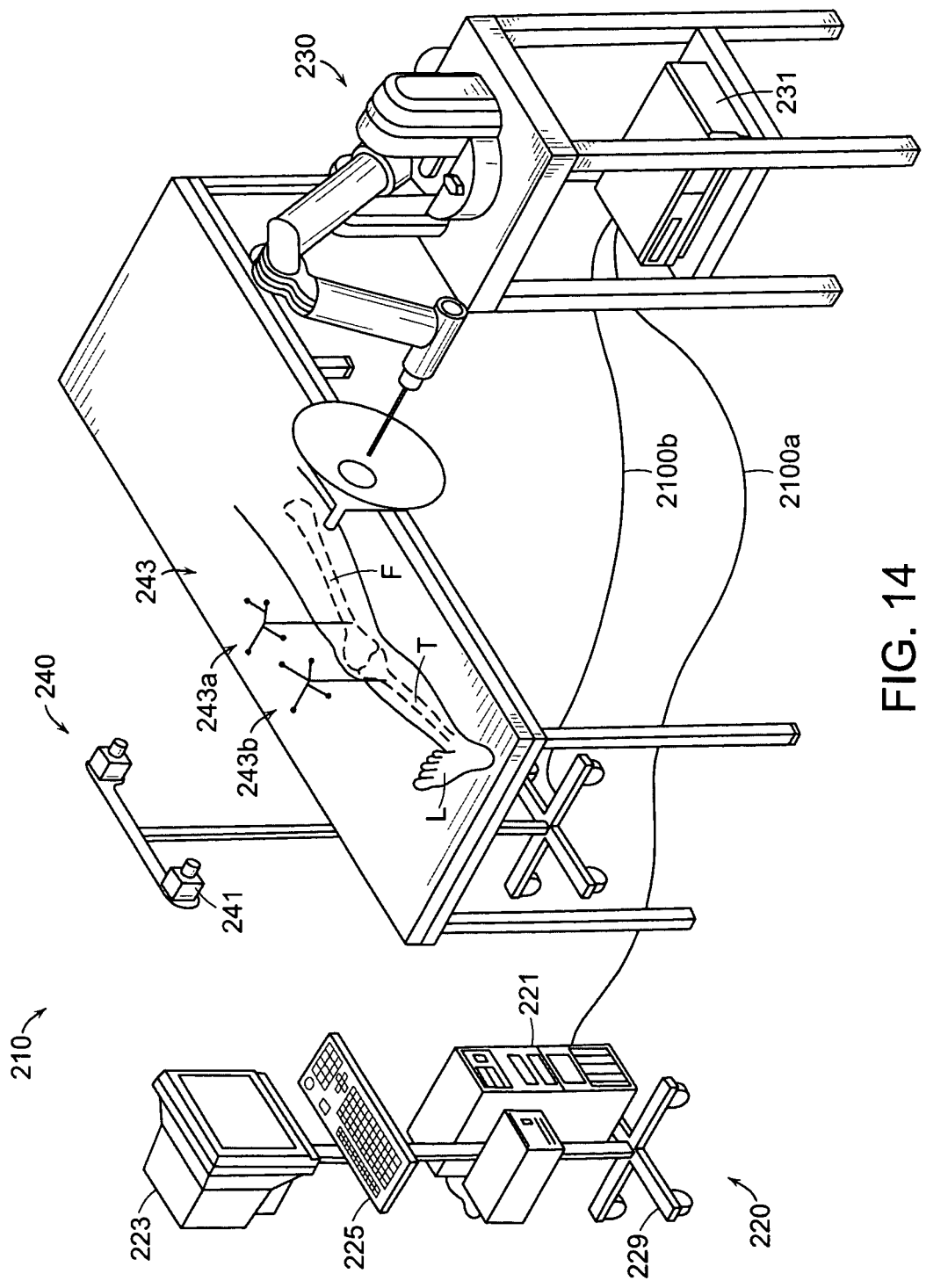
FIG. 14 illustrates an exemplary surgical computer system for implant planning using captured joint motion information.

FIG. 14 shows an embodiment of an exemplary surgical computer system 210 in which the techniques described above can be implemented. Such an exemplary system is described in detail, for example, in U.S. Patent Application Publication No. 2006/0142657, published Jun. 29, 2006, which is hereby incorporated by reference herein in its entirety. In a preferred embodiment, the surgical computer system is the TACTILE GUIDANCE SYSTEM™ or the RIO™, manufactured by MAKO Surgical Corp., Fort Lauderdale, Fla. The surgical system 210 includes a computing system 220, a haptic device 230, and a tracking (or localizing) system 240. In operation, the surgical system 210 enables comprehensive, preoperative and/or intraoperative surgical planning. The surgical system 210 also provides haptic guidance to a user (e.g., a surgeon) and/or limits the user's manipulation of the haptic device 230 as the user performs a surgical procedure. Although included for completeness in the illustrated embodiment, the haptic device 230 and its associated hardware and software is not necessary to perform the techniques described herein.

The computing system 220 includes hardware and software for operation and control of the surgical system 210. Such hardware and/or software is configured to enable the system 210 to perform the techniques described herein. In FIG. 14, the computing system 220 includes a computer 221, a display device 223, and an input device 225. The computing system 220 may also include a cart 229.

The computer 221 may be any known computing system but is preferably a programmable, processor-based system. For example, the computer 221 may include a microprocessor, a hard drive, random access memory (RAM), read only memory (ROM), input/output (I/O) circuitry, and any other well-known computer component. The computer 221 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 221 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The display device 223 is a visual interface between the computing system 220 and the user. The display device 223 is connected to the computer 221 and may be any device suitable for displaying text, images, graphics, and/or other visual output. For example, the display device 223 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 223 may be disposed on or near the computer 221 (e.g., on the cart 229 as shown in FIG. 14) or may be remote from the computer 221 (e.g., mounted on a wall of an operating room or other location suitable for viewing by the user). The display device 223 is preferably adjustable so that the user can position/reposition the display device 223 as needed during a surgical procedure. For example, the display device 223 may be disposed on an adjustable arm (not shown) that is connected to the cart 229 or to any other location well-suited for ease of viewing by the user. The display device 223 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

In addition to the display device 223, the computing system 220 may include an acoustic device (not shown) for providing audible feedback to the user. The acoustic device is connected to the computer 221 and may be any known device for producing sound. For example, the acoustic device may comprise speakers and a sound card, a motherboard with integrated audio support, and/or an external sound controller. In operation, the acoustic device may be adapted to convey information to the user. For example, the computer 221 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 225 of the computing system 220 enables the user to communicate with the surgical system 210. The input device 225 is connected to the computer 221 and may include any device enabling a user to provide input to a computer. For example, the input device 225 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 220 is coupled to a computing device 231 of the haptic device 230 via an interface 2100a and to a detection device 241 via an interface 2100b. The interfaces 2100a and 2100b can include a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 221 and/or the computer 231. In some embodiments, computer 221 and 231 are the same computing device.

The system 210 also includes a tracking (or localizing) system 240 that is configured to determine a pose (i.e., position and/or orientation) of one or more objects to detect movement of the object(s). The tracking system 240 can be used, for example, to track movement of anatomy and/or surgical tools during a surgical procedure and/or to track the pose of the femur F and the tibia T as the joint 120 is moved through a range of motion. In some embodiments, the tracking system 240 may include a detection device (e.g., the detection device 241) that obtains a pose of an object with respect to a coordinate frame of reference of the detection device. As the object moves in the coordinate frame of reference, the detection device tracks the pose of the object to detect (or enable the surgical system 210 to determine) movement of the object. As a result, the computing system 220 can capture data in response to movement of the tracked object or objects. Tracked objects may include, for example, tools/instruments, patient anatomy, implants/prosthetic devices, and components of the surgical system 210. Using pose data from the tracking system 240, the surgical system 210 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 221 and/or the computer 231. For example, utilizing pose data from the tracking system 240, the surgical system 210 is able to associate the physical anatomy (i.e., physical space) with a representation of the anatomy (such as an image displayed on the display device 223) (i.e., image space). Based on tracked object and registration data, the surgical system 210 may determine, for example, a spatial relationship between the image of the anatomy and the relevant anatomy (i.e., between the image space and the physical space).

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). The computer system 210 may also include a coordinate transform process for mapping (or transforming) coordinates in one space to those in another to achieve spatial alignment or correspondence. For example, the surgical system 210 may use the coordinate transform process to map positions of tracked objects (e.g., patient anatomy, etc.) into a coordinate system used by a process running on the computer 231 and/or the computer 221. As is well known, the coordinate transform process may include any suitable transformation technique, such as, for example, rigid-body transformation, non-rigid transformation, affine transformation, and the like.

The tracking system 240 may be any tracking system that enables the surgical system 210 to continually determine (or track) a pose of the relevant anatomy of the patient. For example, the tracking system 240 may comprise a non-mechanical tracking system, a mechanical tracking system, or any combination of non-mechanical and mechanical tracking systems suitable for use in a surgical environment. The non-mechanical tracking system may include an optical (or visual), magnetic, radio, fiber optic, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

In some embodiments, as shown in FIG. 14, the tracking system 240 includes a non-mechanical tracking system. In this embodiment, the non-mechanical tracking system is an optical tracking system that comprises a detection device 241 and at least one trackable element (or tracker) configured to be disposed on (or incorporated into) a tracked object and detected by the detection device 241. In FIG. 14, the detection device 241 includes, for example, a stereo camera pair sensitive to infrared radiation and positionable in an operating room where the surgical procedure will be performed. The tracker is configured to be affixed to the tracked object in a secure and stable manner and includes an array of markers (e.g., an array S1 in FIG. 15) having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 241 detects positions of the markers, and the unique geometry (or firing pattern) and known geometric relationship to the tracked object enable the surgical system 210 to calculate a pose of the tracked object based on the positions of the markers.

The non-mechanical tracking system may include a trackable element (or tracker) for each object the user desires to track. For example, in some embodiments, the non-mechanical tracking system includes anatomy trackers 243a and 243b, generally 243 (to track patient anatomy).

Figure 15:
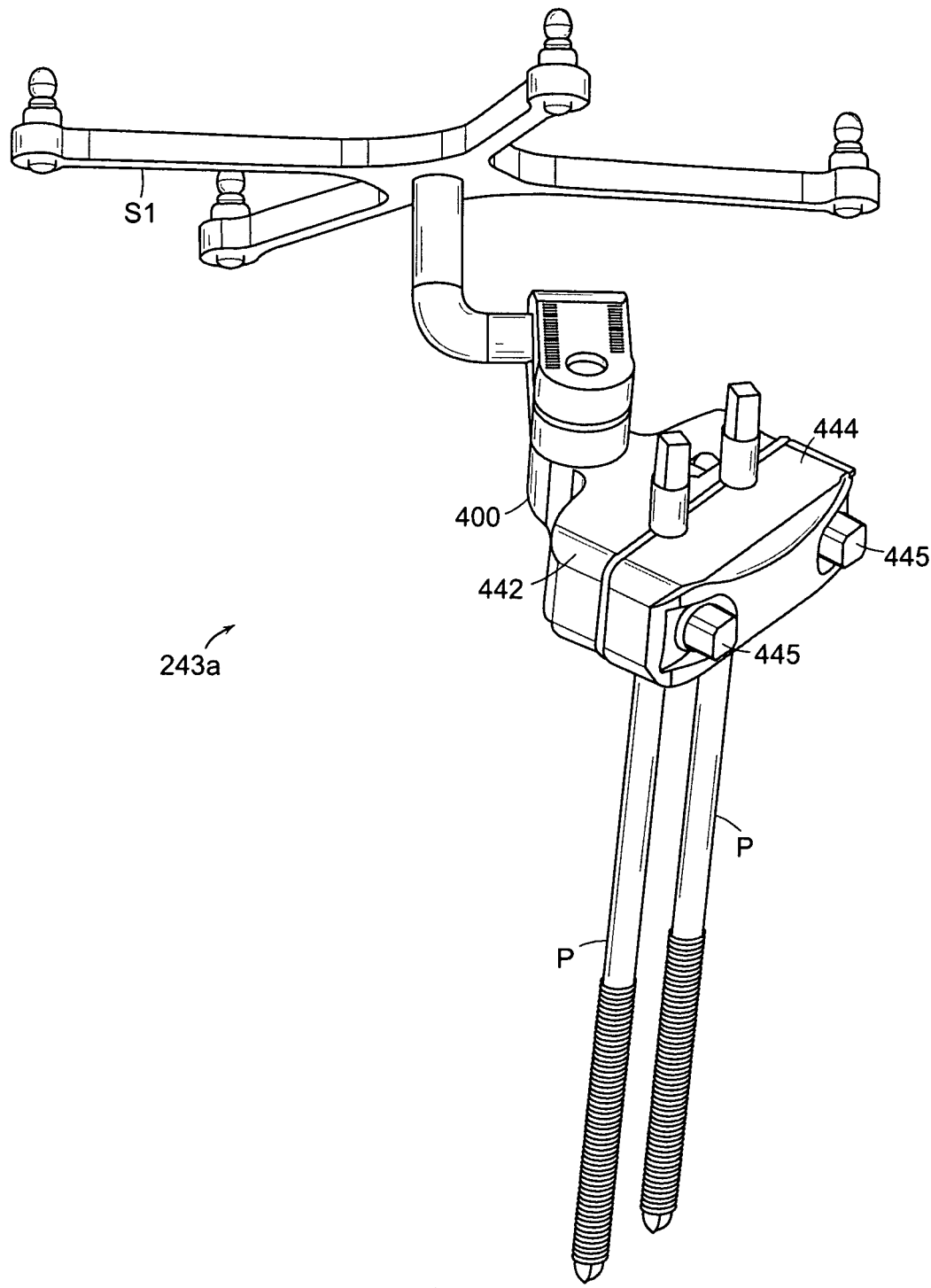
FIG. 15 illustrates an exemplary tracker used by the surgical computer system for implant planning using captured joint motion information.

In FIG. 14, the anatomy tracker 243 is disposed on a relevant portion of a patient's anatomy (such as a bone) and is adapted to enable the relevant anatomy to be detected and tracked by the detection device 241. The anatomy tracker 243 includes a fixation device for attachment to the anatomy. The fixation device may be, for example, a bone pin, surgical staple, screw, clamp, wearable device, intramedullary rod, or the like. In some embodiments, the anatomy tracker 243 is configured for use during knee replacement surgery to track the femur F and the tibia T of the patient. In this embodiment, as shown in FIG. 14, the anatomy tracker 243 includes a first tracker 243a adapted to be disposed on the femur F and a second tracker 243b adapted to be disposed on the tibia T. FIG. 15 illustrates the first tracker 243a, which includes a fixation device comprising bone pins P and a unique array SI of markers (e.g., reflective spheres). The array S1 is affixed to a connection mechanism 400 that is adapted to be removably secured to both of the bone pins P. For example, as shown in FIG. 15, the connection mechanism 400 may include a first portion 442, a second portion 444, and screws 445. To install the first tracker 43a on the femur F, the user screws the bone pins P into the femur F, slides the connection mechanism 400 over the bone pins P, and tightens the screws 445 to draw the first and second portions 442 and 444 together to thereby securely fix the connection mechanism 400 to the bone pins P. Once secured, the connection mechanism 400 imparts additional stability to the bone pins P. The second tracker 243b is identical to the first tracker 243a except the second tracker 243b is installed on the tibia T and has its own unique array of markers. When installed on the patient, the first and second trackers 243a and 243b enable the detection device 241 to detect a pose and track motion of the femur F and the tibia T. As a result, the surgical system 210 is able to detect and capture bone motion in real-time as an individual moves his or her joint through its range of motion.

Figure 16:
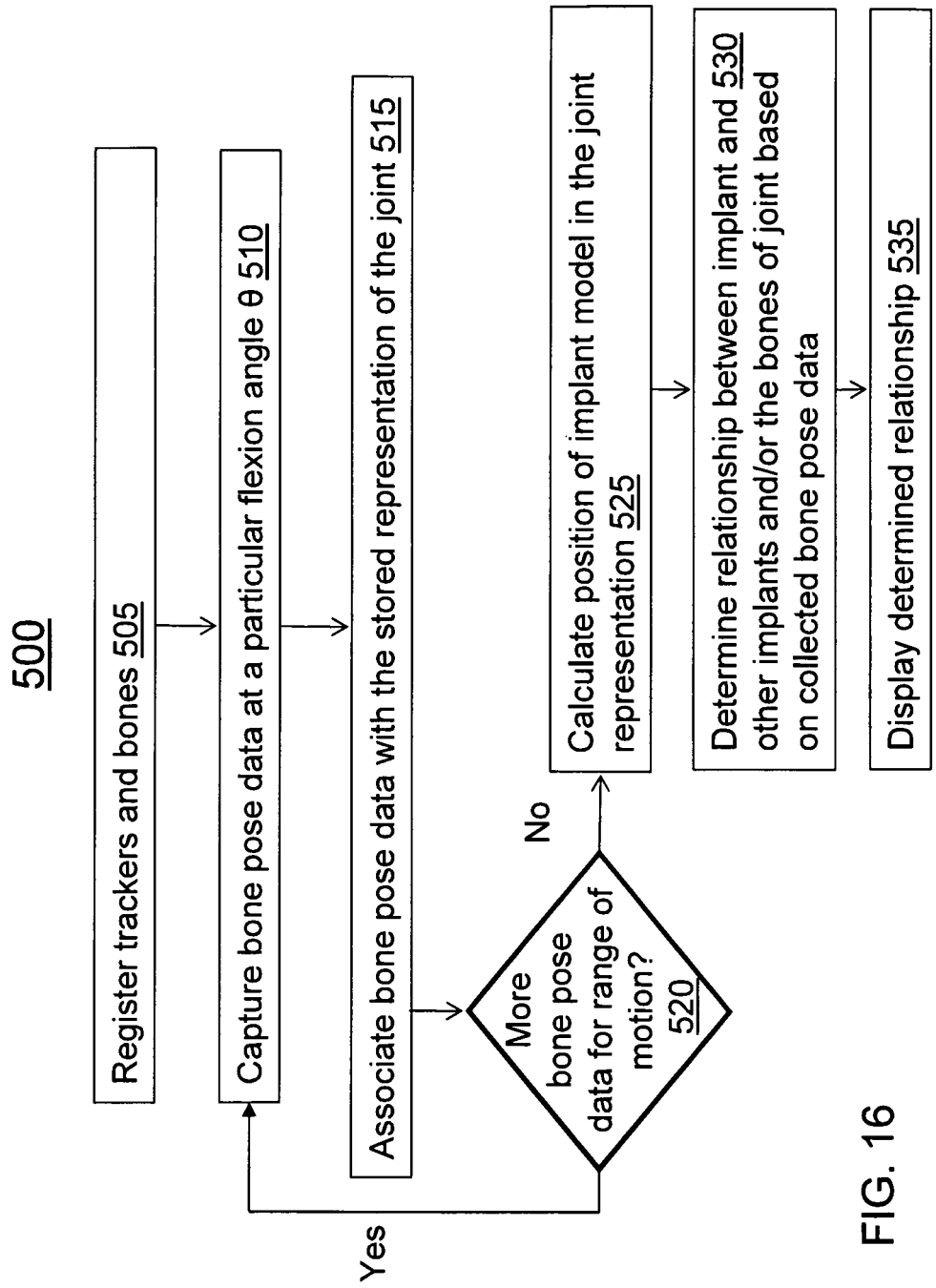
FIG. 16 illustrates an exemplary method for implant planning using captured joint motion information.

FIG. 16 illustrates an exemplary computerized process 500 for implant planning using captured joint motion information. In describing the process 500, the exemplary system 210 of FIG. 14 will be used. In FIG. 14, trackers 243a and 243b are affixed to the femur F and the tibia T, respectively. After these trackers are securely attached to the bones of the knee joint 120, the trackers and the bones are registered (505) using the tracking system 240 and the computing system 220. Once registered, the computing system 220 captures (510) bone pose data (i.e., from the tracking system 240) of the femur F and the tibia T at a particular pose, such as a flexion angle θ of zero degrees (i.e., full extension). Capturing data refers to recording or storing the data, at least on a temporary basis. Capturing can also refer to the detection of the pose data, for example, through the use of trackers and a detection device, and the transmission of that data to its storage location or some processing device that uses the data. Although bone pose data (i.e., position and/or orientation data) is captured in the process 500, it is not necessary to use all captured bone pose data in all embodiments. For example, some embodiments, including embodiments using the system 210, can use less than all of the pose data, for example, only pose data for one or more designated joint flexion angles, to implement the techniques described herein.

In the process 500, for example, using the transform process as described above, the computing system 220 associates (515) the bone pose data with the one or more stored representations of the bones of the joint. These representations can include images and/or models of the bones (e.g., derived from segmented CT data) that have been generated for the particular individual for which the bone pose data is being captured (510).

The computing system 220 can optionally be programmed to determine (520) whether any additional bone pose data is needed for the range of motion. This can be automated, for example, by having a set of predetermined joint flexion angles at which data is collected. If data has not been taken at each of the predetermined flexion angles, the computing system 220 determines (520) that additional bone pose data is needed and displays or otherwise communicates to the operator the next limb pose (e.g., flexion angle θ) to which the joint should be positioned. Upon indication by the operator that the joint is at the indicated pose, the computing system 220 communicates with the tracking system 240 to retrieve the bone pose data and repeats steps 510 and 515. In addition or as an alternative to the set of predetermined poses, the computing system 220 can, through an interface (e.g., displayed text, voice synthesis, etc.), ask the operator whether there are any additional poses (or angles) at which data should be taken. Typically, there are at least two angles (or poses) at which data is captured to calculate the relative poses of the bones through a range of motion of the joint. In a preferred embodiment, data is taken at 10, 40, 60, and 90 degrees of flexion.

If there are no more poses (e.g., angles) at which data needs to be captured, the computing system 220 can calculate (525) the position of the implant model in the joint representation. Such a calculation can take into account input from the user. More specifically, the user of system 220 can, for example through the use of a GUI, manipulate the placement of the implant within the joint representation. Using the implant position and the captured bone pose data, or some derivative thereof, the computing system 220 can determine (530) the relationship (e.g., a physical distance) between, for example, the boundaries of the implant model relative to other implant boundaries and/or relative to the boundaries of one or more bones of the joint. The computing system 220 displays (535) the determined relationship. As described above, there are many ways in which the determined relationship can be displayed, such as a measurement, a graph of the measurement at some or all joint pose angles, a visual representation of the implant and joint, and mapped points.

Figure 17:
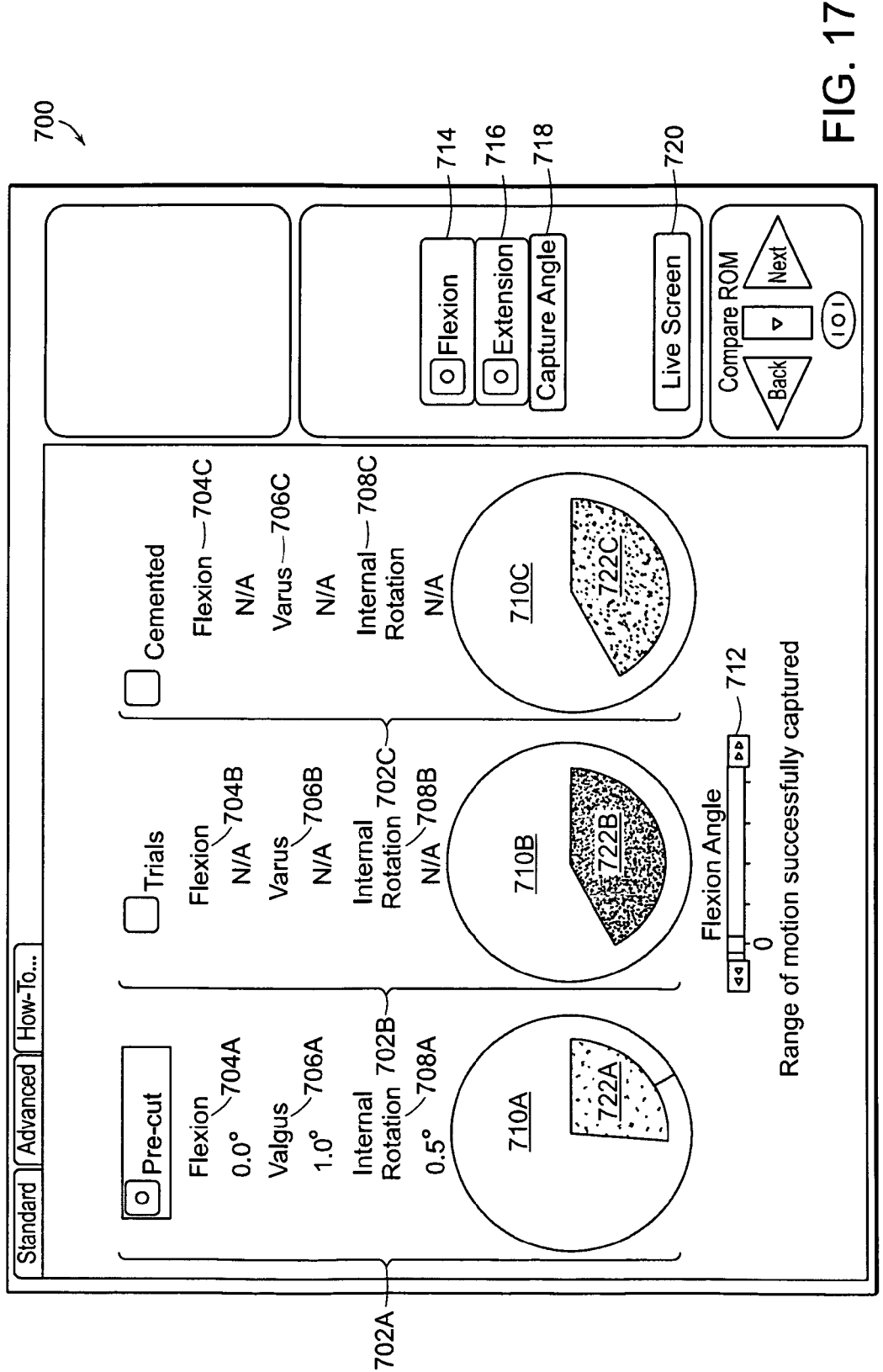
FIG. 17 illustrates an exemplary display for use while capturing corrected limb poses.

FIG. 17 illustrates an exemplary display 700 for use while capturing corrected limb poses (e.g., of the knee joint 120 subject to the corrective force 170 as shown in FIG. 1(d)). The display 700 enables a user to select one or more flexion angles at which a corrected limb pose is to be captured by the computer (e.g., the computer 221). In this example, the display 700 includes a pre-cut display section 702A, a trials display section 702B, and a cemented display section 702C (collectively, display sections 702). In some embodiments, the pre-cut display section 702A can be used to capture pose data before the bones are cut, the trials display section 702B can be used to capture pose data after at least one bone has been cut and one or more temporary trial implants have been installed on the bone, and the cemented display section 702C can be used to capture pose data after at least one bone has been cut and one or more of the actual implants have been cemented to the bone. In another embodiment (not shown) limb poses can be captured with a "closing" force (e.g., a varus moment for a medial disease pathology) to document the extent of the medial compartment degradation. This information can be simultaneously displayed with poses captured under the condition of the corrective forces in order to document the degradation and facilitate differential visualization of the extent of the correction being considered. Each display section 702 includes a flexion/extension indicator (704A, 704B, 704C, collectively 704), a varus/valgus indicator (706A, 706B, 706C, collectively 706), an internal/external rotation indicator (708A, 708B, 708C, collectively 708), and a capture indicator (710A, 710B, 710C, collectively 710). Display 700 includes flexion angle indicator 712, a flexion selector 714, an extension selector 716, a capture angle button 718, and a live screen button 720.

The capture indicators 710 include a captured pose indicator (722A, 722B, 722C, collectively 722). The captured pose indicator can indicate, for example, one or more pose angles at which joint motion data can be captured. Pose data can be captured discretely with the limb in one or more particular poses and/or continuously as the joint moves through a range of motion. For example, in some embodiments, bone pose data for a first pose can be captured discretely with the leg at a first angle of flexion (e.g., full extension), bone pose data for a second pose can be captured discretely with the leg at a second angle of flexion (e.g., full flexion), and/or bone pose data for a range of poses can be captured continuously as the leg is moved from the first angle of flexion to the second angle of flexion. For a knee joint, the captured pose indicators 722 can accommodate the particular patient's F/E ROM. The captured pose indicators 722 can be color coded to facilitate identification of captured poses. For example, the captured pose indicators 722 can be allocated an initial color (e.g., red), and as bone pose data for the indicated poses are captured for the particular joint (e.g., the joint 120), the corresponding pose indicator can be changed to a second color (e.g., green). The resulting captured bone pose data enables the surgeon to see, for each flexion angle θ at which corrected pose data has been captured, the appropriate relative positions of the femur F and the tibia T when they are oriented in the appropriate alignment with appropriate ligament tension. Based on the captured corrected pose data, the surgeon can then use virtual images of the bones and implant models (e.g., as described herein) to plan the placement of the implants in the joint 120 so that, at the various flexion angles, the appropriate relative bone positions with appropriate ligament tension are achieved when the actual implants are implanted in the joint 120.

Figure 18:
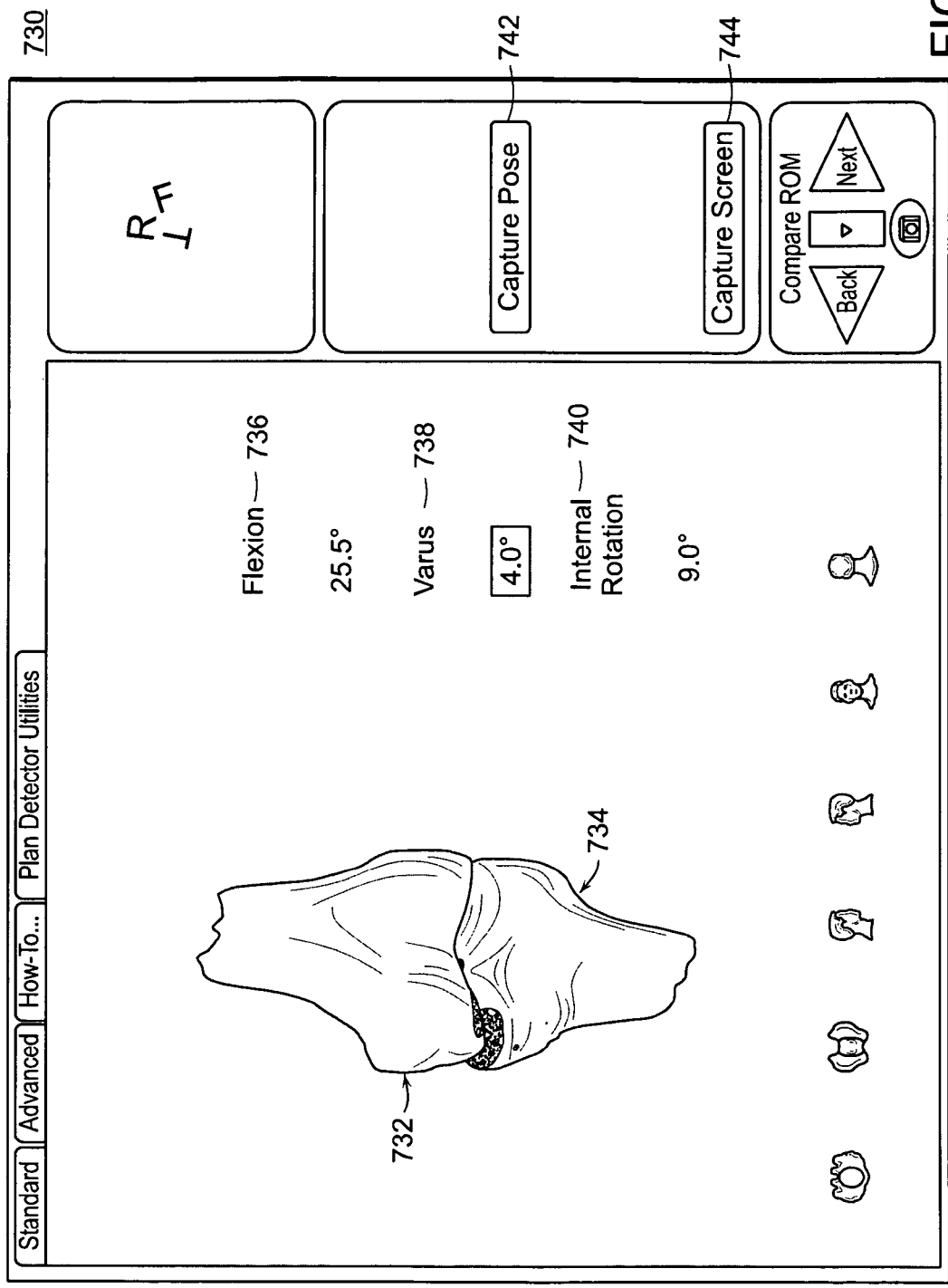
FIG. 18 illustrates an exemplary display for a live joint angle data display screen.

FIG. 18 illustrates an exemplary display for a live joint angle data display screen 730. In this exemplary embodiment, the live joint angle data display screen 730 provides real-time 3D joint poses of the subject patient. The live joint angle data display screen 730 includes a representation of the femur 732 and a representation of the tibia 734. The live joint angle data display screen 730 includes a flexion/extension indicator 736, a varus/valgus indicator 738, an internal/external rotation indicator 740, a capture pose button 742, and a capture screen button 744.

Figure 19:
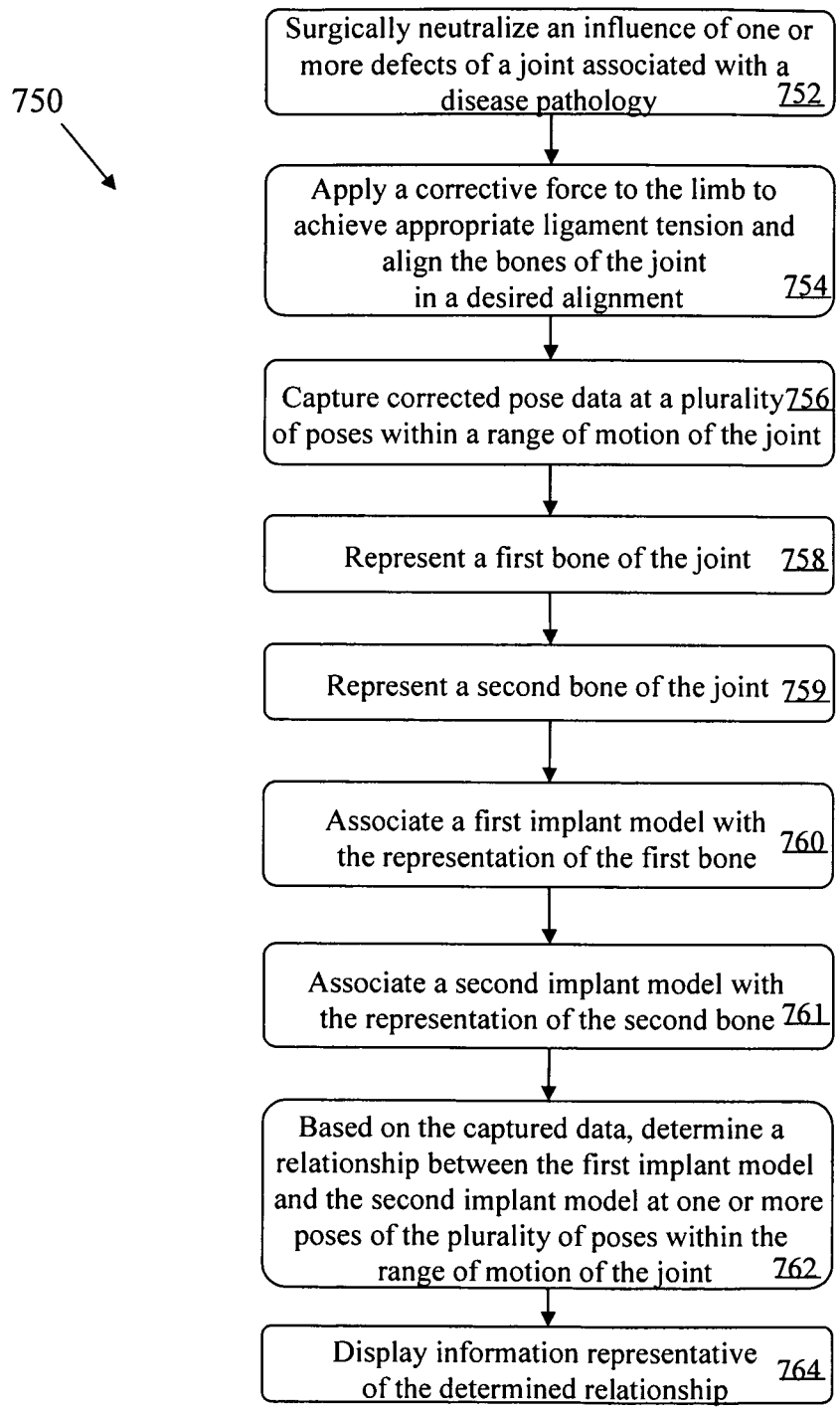
FIG. 19 illustrates an exemplary method for displaying a relationship between an implant model and a representation of a bone.

FIG. 19 illustrates an exemplary method 750 for displaying a relationship between a first implant model and a second implant model. The influence of one or more defects of a joint (e.g., the joint 120) associated with a disease pathology are surgically neutralized (752). A corrective force (e.g., the corrective force 170) is applied (754) to the limb (e.g., the leg) to simultaneously achieve appropriate ligament tension and align the bones (e.g., the femur F and the tibia T) of the joint in a desired alignment. Data representative of the bone poses when the limb is subject to the corrective force (i.e., corrected pose data) is captured (756) at a plurality of poses (e.g., flexion angles) within a range of motion of the joint. The first bone of the joint is represented (758) (e.g., via the implant planning display 820 of FIGS. 22(*a*) through 22(*c*)). The second bone of the joint is also represented (759). A first implant model is associated (760) with the representation of the first bone. A second implant model is associated (761) with the representation of the second bone. Based on the captured corrected pose data, a relationship is determined (762) between the first implant model and the second implant model through at least one or more poses of the plurality of poses within the range of motion of the joint (e.g., through at least a portion of the range of motion of the joint). Information representative of the determined relationship is displayed (764). Steps 756-764 can be performed, for example, by the computer 221, or one or more other computing devices.

The captured pose data can be utilized during implant planning to determine how to position and orient implant components in the joint 120. As discussed above, the bone pose data can be acquired (e.g., preoperatively and/or intraoperatively) prior to implant planning. For example, the corrective force 170 is applied so the leg is corrected (754) to a desired alignment with appropriate ligament tension, the corrected bone poses are captured (756), and implant planning is performed based on the captured data. Advantageously, after implantation of physical implant components that correspond to the implant models, the limb achieves the desired alignment and appropriate ligament tension in accordance with the virtual implant plan. In a preferred embodiment, bone pose data capture and implant planning are accomplished intraoperatively and are based, not on simulated computer data, but on numerical data of the patient's actual bones (e.g., in graphical model form) representing the patient's actual joint geometry as the joint physically moves through a range of motion.

With respect to step 752, the captured data should not be erroneously influenced by effects of a disease pathology (e.g., an oestoarthritis pathology with osteophytes, capsular adhesions, and/or OCDs). The influence of any defects can be surgically neutralized. For example, any existing osteophytes that interfere with medial collateral ligament (MCL) function are removed. Similarly, capsular adhesions that interfere with knee function are relieved. With the influence of any defects surgically neutralized, correct leg kinematics can be achieved by applying a corrective force to the leg through full range of motion of the joint thereby compensating for the defects.

With respect to step 754 and FIGS. 1(*d*)-(*g*), to achieve kinematics correcting for disease pathology defects, the joint 120 bones (e.g., the femur F and/or the tibia T) should be spaced as if there was no defect 160 (e.g., with the MCL 162 and LCL 164 properly tensioned and with limb alignment corrected). In some examples, CT-derived models (e.g., representations of bones, representations of implant components, etc.) can not be obtained for a diseased joint in the desired alignment before performing step 752. Surgically neutralizing the influence of one or more defects and applying the corrective force 170 can provide correct bone spacing (e.g., extension and flexion gaps) when the limb in the desired alignment with appropriate ligament tension. This information can be used during implant planning (e.g., based on the captured data). As a result, after resection and component implantation, the femur F and the tibia T will articulate as intended resulting in a postoperative performance of the joint 120 that yields the desired limb alignment concurrently with properly balanced ligaments throughout the range of motion of the joint.

With further respect to step 754, in some embodiments with the joint 120 comprising regions of bone/cartilage deficiency, the corrective force 170 can induce a varus and/or valgus moment (e.g., the valgus moment 174) on the joint 120 to properly tension the collateral ligaments. However, one can appreciate that the proper restoration is dictated by patient specific characteristics and may vary. As discussed above, the magnitude of the corrective force 170 should be sufficient to restore the anatomy of the joint 120 so that the limb achieves a desired alignment (e.g., with the tibia T and the femur F aligned within an acceptable range of a neutral mechanical axis 172) with appropriate ligament tension. For example, for a medial unicondylar knee replacement, if the magnitude of the corrective force 170 and/or the resulting displacement (e.g., as shown in FIG. 1(*e*)) are insufficient (e.g., too little), the MCL 162 can be loose and the medial compartment can be overloaded, which increases the risk of postoperative implant loosening. In contrast, if the magnitude of the corrective force 170 and/or the resulting displacement are excessive (e.g., too great), the MCL 162 can be tight and the lateral compartment can be overloaded, which increases the risk of postoperative disease progression to the lateral compartment of the joint.

Figure 20:
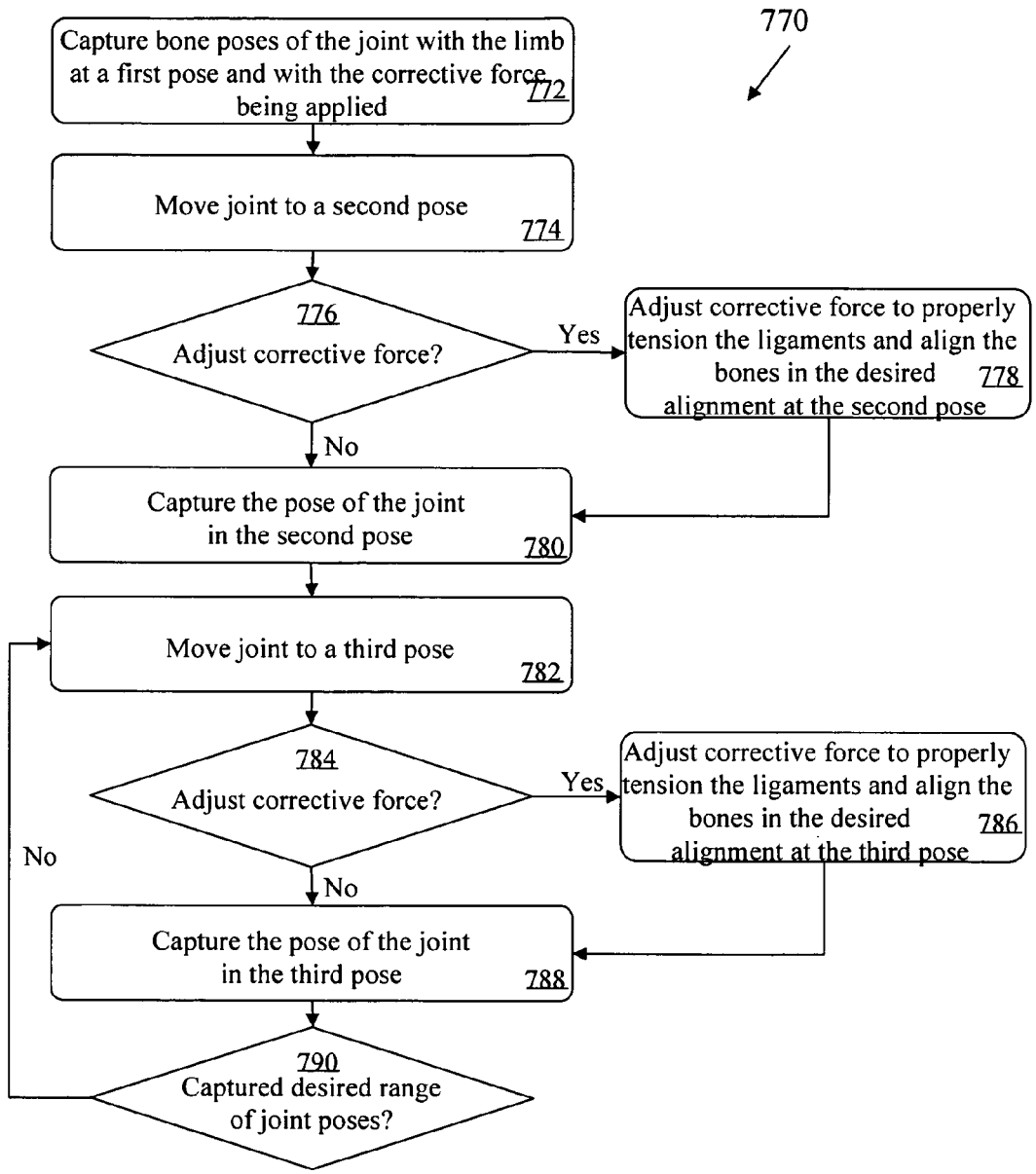
FIG. 20 illustrates an exemplary method for capturing data representative of corrected poses during a range of motion of a joint in further detail of FIG. 19.

FIG. 20 illustrates an exemplary method for capturing corrected bone pose data at a plurality of poses within a range of motion of a joint in further detail of step 756 of FIG. 19. The bone poses of the joint (e.g., joint 120) with the limb at a first pose (e.g., full extension with a joint flexion angle $\theta=0°$ as shown in FIG. 2) and with the corrective force being applied are captured (772). The joint is moved (774) to a second pose (e.g., full flexion with the joint in its maximum flexion range, e.g., $\theta=150°$ as shown in FIG. 2). If the corrective force needs to be adjusted (776) to properly tension the ligaments and align the bones in the desired joint alignment at the second pose, the corrective force is adjusted (778). The bone poses are captured (780) at the second pose. The joint is moved (782) to a third pose. If the corrective force needs to be adjusted (784), the corrective force is adjusted (786) to properly tension the ligaments and align the bones in the desired alignment at the third pose. The bone poses are captured (788). If the desired range of joint poses is not captured (790), the system proceeds back to step 782 and repeats for additional poses.

Capturing bone pose data throughout the range of motion of a joint allows for accurate implant planning. For example, the surgeon can adapt the implant plan based on the changing relationships among the femur F, the tibia T, and the soft tissue ligaments as the joint moves through a range of motion. Additionally, because all bone models and captured pose data are based on the patient's actual physical anatomy and joint kinematics (as opposed, e.g., to simulated and/or interpolated data), the implant plan is customized to the patient's unique anatomy and joint movement. With the corrective force applied so that the ligaments are adequately tensioned and limb alignment is passively corrected, the bone poses are captured. Bone poses can be captured in any sufficient manner. For example, referencing FIG. 17, in some embodiments (which is not intended to be limiting), the leg is moved to a first extension point (e.g., full extension, a flexion angle $\theta$ of 0° to 10°), the extension selector 716 is selected, and the pose is captured by clicking the capture angle button 718. The leg is then moved to first flexion point (e.g., full flexion, a flexion angle $\theta$ of 115°), the flexion selector 714 is selected, and the pose is captured by clicking the capture angle button 718. In this embodiment, the first extension point of the joint and the first flexion point of the joint represent the starting and ending points of the captured pose indicator 722. For example, the captured pose indicator spans a portion of the circumference of the capture indicator 710 indicative of an angle between the first extension point and the first flexion point of the joint (e.g., 150° between pose 176A and pose 176C for joint 120 of FIG. 2). Optionally, bone pose data can also be captured continuously as the joint is moved from the starting point to the ending point of the captured pose indicator 722. Additionally, the first flexion point and the first extension point can be any two angles within the range of motion of the joint.

With respect to step 776, if the articular surfaces of the joint are contacting healthy cartilage in this pose (e.g., in the pose the defect 160 is not negatively affecting the joint and the joint is in a proper joint alignment), the ligaments may be properly tensioned naturally. Therefore, in some embodiments, depending on the pose and the anatomy of the joint, it may not be necessary to apply the corrective force 170 for one or more poses of the joint throughout the range of motion. If, for example, the posterior condyle has an osteochondral deficit, a slight, but sufficient, distraction of the medial compartment in flexion (e.g., through a reduced corrective force 170) can achieve the desired alignment (e.g., a corrected pose) with the MCL 162 appropriately tensioned.

With respect to steps 784 through 790, poses for any additional desired flexion angles in the remainder of the range of motion of the joint are captured. For example, referencing FIG. 2, after capturing the full flexion pose 176C at 150°, any desired remaining poses from 150° to the full extension pose 176A at 0° can be captured either discretely, by moving the joint to the desired pose and capturing pose data, or continuously, by slowly bring the leg back into extension as the system captures pose data (e.g., at specified degree intervals). Any number of poses can be captured by the system. As explained above, the magnitude of the corrective force required to restore the joint to the desired alignment and appropriate ligament tension can vary for each desired joint pose (e.g., due to the influence of one or more defects of the disease pathology of the joint). For example, a corrective force of a first magnitude is applied to the joint at a first pose (e.g., flexion angle) to correct the tension of one or more ligaments associated with the joint, while a corrective force of a second magnitude is applied to the joint at a second pose (e.g., flexion angle) to correct the tension of the one or more ligaments. Thus, the magnitude of the corrective force is adjusted as necessary for poses to maintain the limb in the desired alignment with appropriate ligament tension. In a preferred embodiment, bone pose data is captured, with the corrective force applied, at (a) an extension pose where the flexion angle $\theta$ is between about 0° to 10°; (b) a flexion pose where the flexion angle $\theta$ is about 90°; (c) a first intermediate pose where the flexion angle $\theta$ is about 40°; and (d) a second intermediate pose where the flexion angle $\theta$ is about 60°.

The bone poses can be captured, for example, using known surgical navigation tracking techniques. Bones can be tracked in any known manner. For example, in some embodiments, at least one trackable element (e.g., a tracker with an array SI of markers as shown in FIG. 15) is configured to be disposed on or incorporated into the femur F and the tibia T. The trackable element is tracked by the detection device 241 (e.g., an optical camera), which continuously determines the pose of the trackable element. Using transforms as is well known, the pose of the trackable element can be used to determine the pose of the bone on which the trackable element is disposed. The tracked bones are registered (i.e., correlated or mapped) to the representations of the bones (e.g., the representation of the first bone 801 and the representation of the second bone 802 of FIGS. 21(a) and 21(b)) so that the poses of the representations 801, 802 correspond to the poses of the respective physical bones. The bone pose data is captured with the system and displayed in virtual planning software (e.g., FIGS. 17, 18 and 22(a)-(c)) so that the pose of one bone relative to the other bone can be readily identified. Any known registration technique can be used. For example, a detailed description of a typical registration process is described in U.S. patent application Ser. No. 11/357,197, (e.g., at paragraphs [0128], [0129], and [0205] of the corresponding U.S. Patent Application Publication No. 2006/0142657) which is hereby incorporated by reference herein in its entirety.

In some embodiments, referencing FIGS. 17 and 18, a live joint angle data display screen 730 can be used to provide real-time 3D knee pose angles. For example, selecting a live screen button 720 produces the display screen 730. The joint can be moved through its angular range (e.g., with the appropriate corrective force applied to the limb throughout the range of motion) to capture corrected joint motion data that can be used to plan implant placement and/or assess how preoperatively planned implant components will interact. In some examples, the corrective force 170 (which induces a valgus moment 174 in the embodiment of FIG. 1(*d*)) is used to align the bones in a desired alignment with a sufficiently tensioned MCL 162 to compensate for any defects. Data can be captured through the user interacting with the display screen 730 and used to aid in intraoperative planning of the implant components within the joint.

FIG. 21(*a*) illustrates an exemplary computer display 950 of a graph of a gap/overlap analysis of the positions of implant models over a range of flexion angles (or poses). As described above with reference to FIG. 9(*a*), the horizontal axis of the graph 950 displays the value of the flexion angle $\theta$ of a corresponding pose (e.g., from $\theta=-10$ to $\theta=90$). The vertical axis of the graph 950 displays the value of the calculated gap or overlap between two measured points (e.g., the first implant model and the second bone, the first implant model and the second implant model, etc.). In the graph 950, bars extending upward from zero in the positive direction of the vertical axis (which can be color coded for identification) represent flexion angles where the two measured points have a gap between them, which might result in a loose knee at those flexion angles (e.g., bars 956A, 956B, and 956C). The bars indicate the distance of the gap in millimeters. Bars extending downward from zero in the negative direction of the vertical axis represent flexion angles where the measured points overlap (e.g., bar 956D at a flexion angle of 90°), which might result in a tight knee at those flexion angles.

Bone poses of the joint 120 can be captured along the range of motion 952 at various flexion angles $\theta$ of the knee joint 120. As described above with reference to FIG. 2, the relative positions of the femur F and the tibia T change as the joint 120 moves through the range of motion resulting in a plurality of limb poses (e.g., pose 954A, 954B, 954C, and 954D, collectively poses 954) throughout the range of motion 952 of the knee joint 120. The pose 954A results when the joint flexion angle $\theta=0°$ (e.g., full extension). The pose 954B results when the joint flexion angle $\theta=40°$. The pose 954C results when the joint flexion angle $\theta=60°$. The pose 954D results when the joint flexion angle $\theta=90°$. Although the exemplary graph 950 includes angles $-10°$ through $\sim 90°$, any range of angles can be displayed. While only four poses 954 are shown, the limb can include any number of poses that can be captured, including poses with the joint 120 in extension beyond the flexion poses 954.

As described herein, the position of one or more implants can be manipulated through the user interface so the surgeon can see the gap/overlap analysis for different implant positions. In such situations, the graph 950 updates as the implant positions are adjusted, which affects the gap or overlap between the two measured points for the pose. With the graph 950, the user (e.g., the surgeon) can advantageously see all gaps and overlaps over the entire range of motion 952 in one display. This enables the user to slightly modify the position of the implant(s) and receive feedback on the modification over the entire range of motion 952. The user can then adjust the position to achieve a desired goal (e.g., minimize all gaps and overlaps, minimize center gaps and overlaps at the expense of larger gaps and overlaps at the ends of the range, etc.).

For example, the four poses 954 can be captured (e.g., using the display 700 to capture the limb poses of the knee joint 120 subject to the corrective force 170 as shown in FIG. 1(*d*)). A gap/overlap value is calculated between the two measured points at each pose 954, resulting in the four bars 956A, 956B, 956C, and 956D, collectively 956. Bars 956A, 956B, and 956C are positive, and therefore represent a gap between the two measured points. The bar 956A indicates that at pose 954A, if the one or more implant components are implanted based on the current implant plan, the two measured points would have a gap between them of approximately 1.1 mm. The bar 956B indicates that at pose 954B (i.e., the joint flexion angle $\theta=40°$), the two measured points have a gap of approximately 0.9 mm using the current implant plan. The bar 956C indicates that at pose 954C the two measured points have a gap of approximately 0.5 mm using the current implant plan. Bar 956D is negative, which indicates that at pose 954D the two measured points have an overlap of approximately 0.5 mm with the current implant plan. The bar 956D indicates that at pose 954D, if the one or more implant components are implanted based on the current implant plan, the two measured points would interfere such that the first and second implants would be compressed together (i.e., a tight knee).

According to an embodiment, implant planning can be accomplished using representations of the femur F and the tibia T in the desired alignment, where the representations of the femur F and the tibia T are based the captured corrected bone pose data. For example, FIG. 21(*b*) shows a detailed perspective view of a representation of a knee joint at a first flexion angle $\theta$ (e.g., 10 degrees) 800B, including a representation of a first bone 801 (e.g., a representation of the femur F), a representation of a second bone 802 (e.g., a representation of the tibia T), a representation of an MCL 162, and a representation of an LCL 164. The representation of the knee joint 800B can be, for example, a virtual representation of the diseased joint 120 shown in FIG. 1(*c*). The representation, however, is based on the bone pose data that was captured when the joint 120 was disposed at the first flexion angle $\theta$ with a corrective force 170 applied to the leg. The corrective force 170 induces a valgus moment 812 that moves the misaligned joint of FIG. 1(*c*) into a desired alignment with appropriate ligament tension, as shown in FIG. 21(*b*). As a result, the representation of the knee joint 800B shows the bones in the desired alignment, and the surgeon can plan implant placement for the first flexion angle $\theta$ based on the relative positions of the bones shown in FIG. 21(*b*). To plan implant placement at the first flexion angle $\theta$, a representation of a first implant component 804 (e.g., a virtual model of a medial femoral condyle implant component) is positioned (e.g., by the surgeon using an implant planning GUI interface) on the representation of the first bone 801. A representation of a second implant component 806 (e.g., a virtual model of a medial tibial implant component) is positioned on the representation of the second bone 802. In some embodiments, the position and orientation of each implant component 804, 806 are adjusted until a gap of between about 0 mm to about 1.25 mm exists between the surfaces of the implant components 804, 806. In a preferred embodiment, the gap is about 1 mm (as discussed further below). As discussed above in connection with the graph 950 of FIG. 21(*a*), once the implant components 804, 806 are initially positioned at the first flexion angle $\theta$, the relative positions of the implant components 804, 806 can be examined at other flexion angles and adjusted as necessary until the implant components 804, 806 are planned so that the resulting gap at each flexion angle $\theta$ falls within a desired range.

Figure 21B:
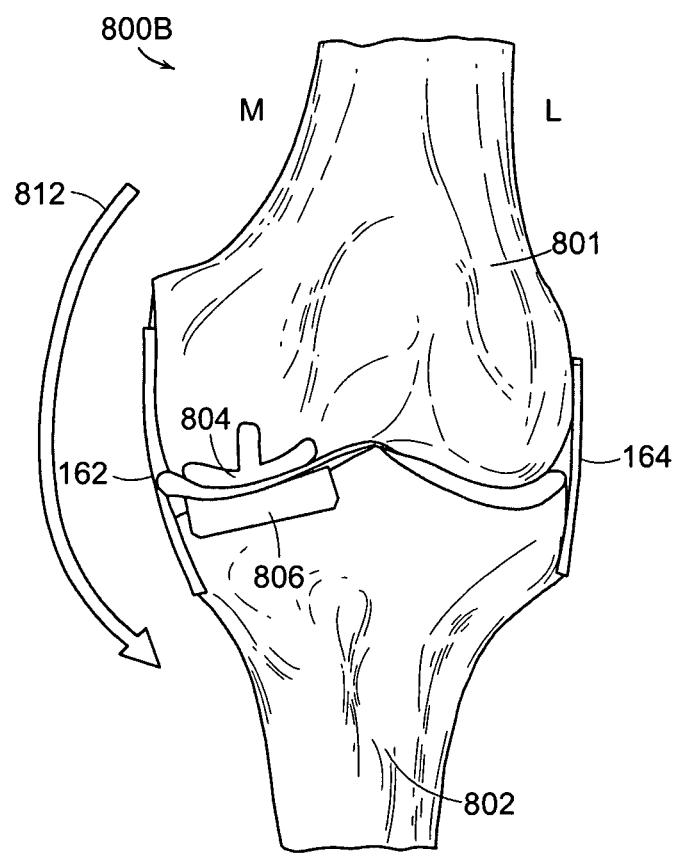
FIG. 21(b) is a detailed perspective view of a knee pose with representations of implant components.
Figure 22A:
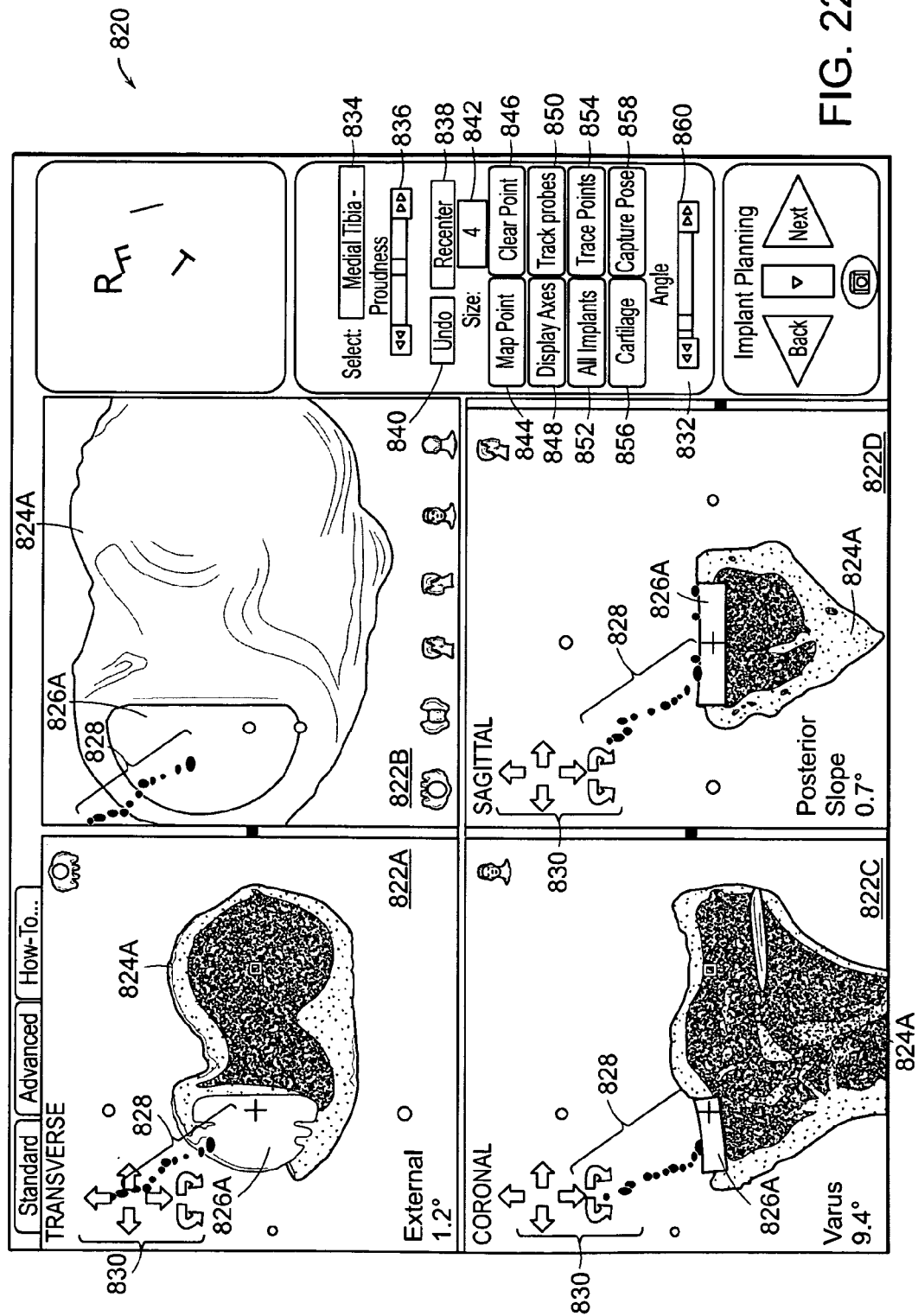
FIGS. 22(a) through 22(c) illustrate an exemplary implant planning display 820.
Figure 22B:
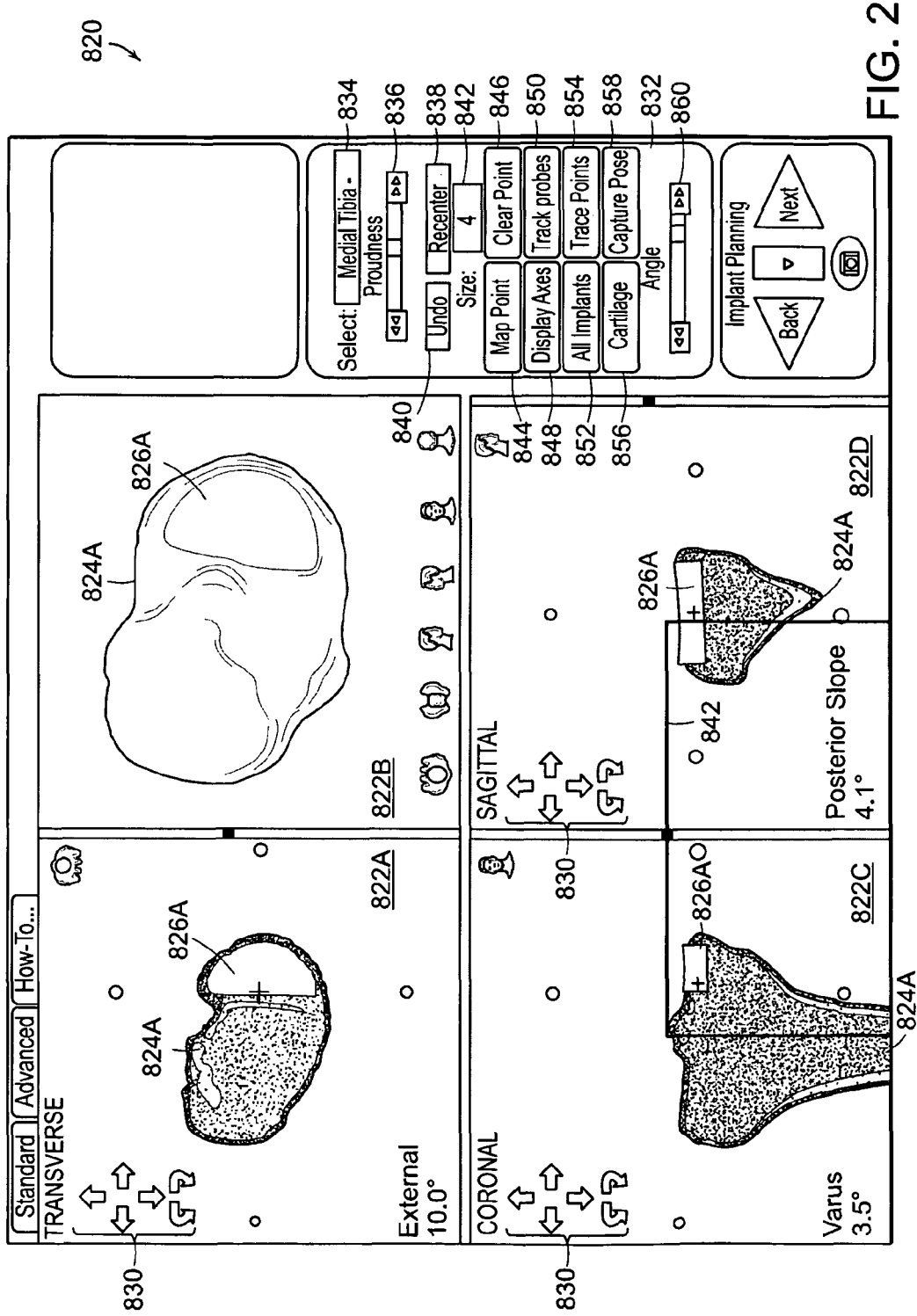
Figure 22C:
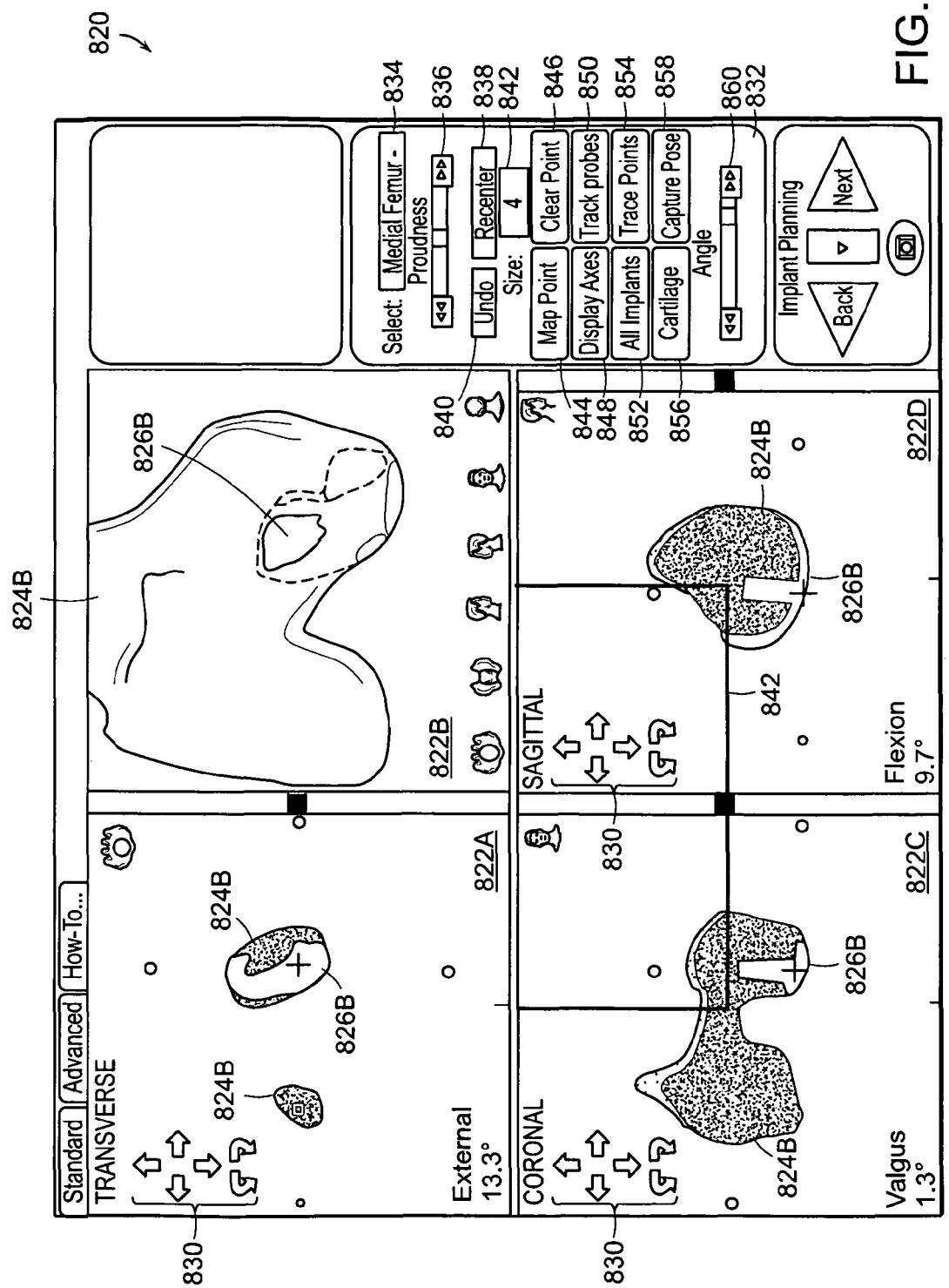

FIGS. 22(*a*)-22(*c*) illustrate an example of an implant planning display 820. The implant planning display 820 is merely one example of an implant planning user interface that can be used and is not intended to be limiting. Any other suitable implant planning system may be used to accomplish the present invention. In the example of FIGS. 22(a)-22(c), the implant planning display 820 enables a user to change a position and/or orientation of a representation of an implant component (e.g., the representation of the first implant component 804 or the second implant component 806) for a selected pose (e.g., a selected flexion angle θ). The implant planning display 820 includes planning sections 822A, 822B, 822C, and 822D (collectively planning sections 822). Planning section 822A is a transverse view, planning section 822C is a coronal view, and planning section 822D is a sagittal view of the representations of the bones and/or the representations of the implant components. In FIGS. 22(a) and 22(b), planning sections 822 include a representation of a tibia 824A (e.g., the representation of the second bone 802 of FIG. 21(b)) and a representation of a tibial implant component 826A. If applicable, the planning sections 822 of FIG. 22(a) may include traced points 828. In FIG. 22(c), planning sections 822 include a representation of a femur 824B (e.g., the representation of the first bone 801 of FIG. 21(b)). In FIGS. 22(a)-22(c), planning sections 822A, 822C, and 822D include implant component movement controls 830. The implant planning display 820 includes a control area 832. The control area 832 can include one or more control features, such as, for example, a bone selector 834, a proudness selector 836, a recenter button 838 (e.g., to change the center of the representation of the tibial implant component 826A from its default location), an undo button 840, a component size selector 842, a map point button 844 (e.g., to map a single point corresponding to the tip of a tracked probe), a clear point button 846, a display axes button 848 (e.g., to show mechanical and/or anatomic axes, such as axes 842 of FIGS. 22(b) and 22(c)), a track probes button 850 (e.g., to allow the viewing of a tracked probe tip position during implant planning), an all implants button 852, a trace points button 854, a cartilage button 856, a capture pose button 858, and/or any other control feature useful to the surgeon in virtually planning placement of the implant components. The control area 832 preferably includes an angle selector 860 (e.g., as described above in connection with FIGS. 5 and 9). FIGS. 22(b) and 22(c) may also include axes 842. FIG. 22(c) includes a representation of a femoral implant component 826B. If applicable, the display 820 may include captured cartilage points and/or a cartilage surface, as described, for example, in U.S. patent application Ser. No. 12/333,119, filed Dec. 11, 2008, which is hereby incorporated by reference herein in its entirety. The display 820 can be used to show any bone for which bone pose data has been captured and any combination of implant components (e.g., via the bone selector 834).

Figure 21A:
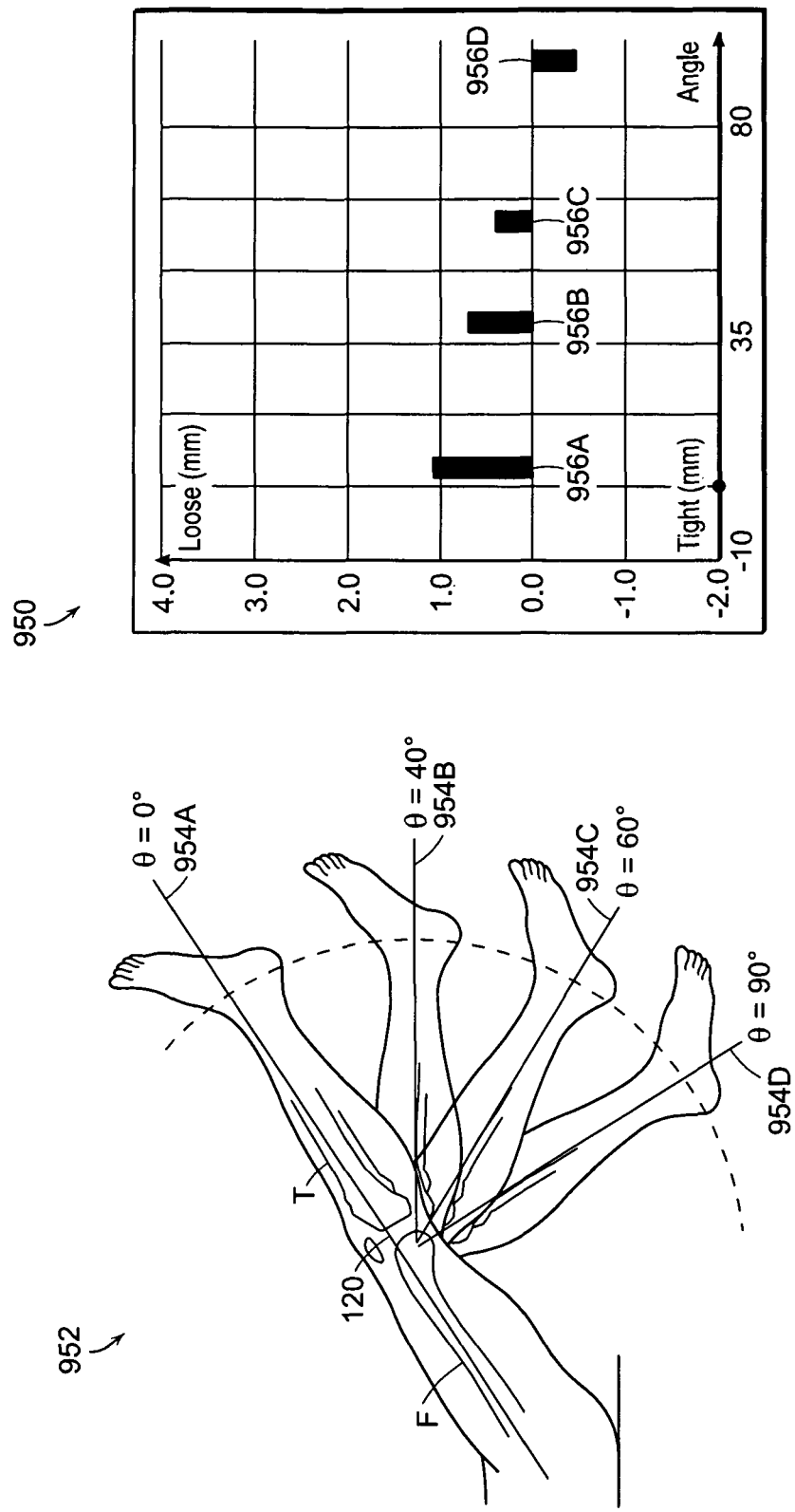
FIG. 21(a) illustrates an exemplary computer display of a graph of a gap/overlap analysis over a range of flexion angles.

As shown in FIGS. 21(a) and 21(b), the interactions of the representations of the first and second implant components can be influenced by limb pose. For example, as discussed above in connection with the graph 950 of FIG. 21(a), the implant components can be separated by a gap (i.e., a loose joint) at one flexion angle θ and overlapping (i.e., a tight joint) at another flexion angle θ (e.g., bar 956A indicates pose 954A has gapped implants at flexion angle θ=0°, while bar 956D indicates pose 954D has overlapping implants at flexion angle θ=90°). One goal of implant planning is to eliminate the possibility of such variation by ensuring that a correct relationship is maintained between the implants at each of the various poses (e.g., flexion angles). A correct relationship may be maintained, for example, by preserving a proper distance between the implant components throughout the range of motion of the joint.

Figure 23:
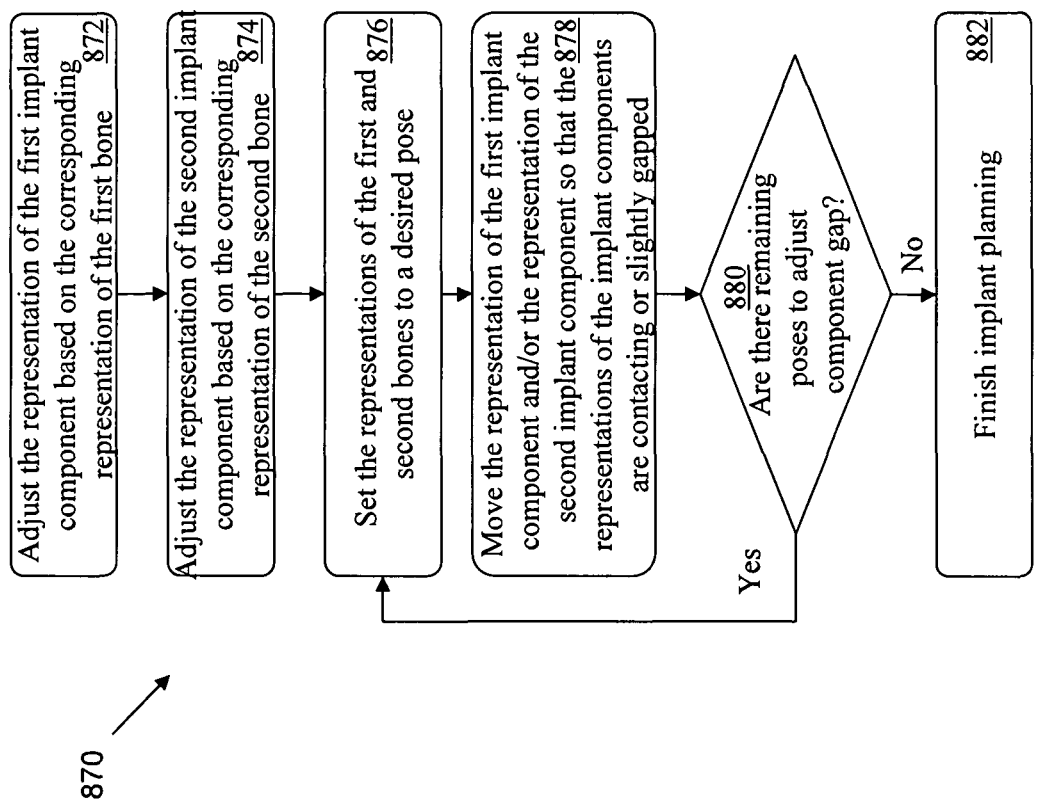
FIG. 23 illustrates an exemplary method for adjusting a distance between two representations of implant components throughout a range of motion of a joint.

FIG. 23 illustrates an exemplary computerized method 870 for adjusting a distance between two representations of implant components (e.g., the representations of the first implant component 804 and the second implant component 806) throughout a range of motion of a joint. The pose (i.e., position and/or orientation) of the representation of the first implant component is adjusted (872) based on the corresponding representation of the first bone (e.g., the representation of the first implant component 804 is adjusted based on the representation of the first bone 801). The pose of a representation of an implant component can be adjusted, for example, using the implant component movement controls 830 of the display 820. The pose of the representation of the second implant component is adjusted (874) based on the corresponding representation of the second bone (e.g., the representation of the second implant component 806 is adjusted based on the representation of the second bone 802). The representations of the first and second bones are set (876) to a desired pose, such as a joint flexion angle θ of full extension (e.g., pose 176A of FIG. 2). The use of full extension as a starting point is illustrative only. Any other starting pose is equally applicable. The representation of the first implant component and/or the representation of the second implant component is moved (878) so that the representations of the implant components are just contacting or slightly gapped. If there are no remaining poses (e.g., flexion angles) at which the component gap should be adjusted (880), implant planning is completed (882). If there are remaining poses (e.g., joint flexion angles) which need the component gap adjusted, steps 876 through 880 are repeated for each remaining pose until completion of implant planning (882).

With respect to steps 876 and 878, a user can set the one or more representations of bones to full extension by setting the angle selector 860 to full extension. The angle selector 860 is similar to the user inputs and indicators described above in connection with FIGS. 5 and 9. The angle selector 860 slide bar can be adjusted to any angle that was captured during the bone pose data capture (See FIGS. 17-20). If limb alignment was corrected (e.g., via the corrective force 170) and the collateral ligaments were concurrently properly tensioned during the bone pose data capture along the range of motion of the joint, the representations of the bones (e.g., the femur F and the tibia T) will be correctly spaced apart, allowing for optimal implant planning. For step 878, the user can, for example, move the representation of the first implant component 804 (e.g., a representation of a femoral implant component) superiorly and/or inferiorly to contact the representation of the second implant component 806 (e.g., a representation of a tibial implant component) or to be slightly gapped. A slight gap distance can be, for example, between the range of 0 mm to 1.25 mm. In a preferred embodiment, the gap distance is about 1 mm. The gap can be estimated, for example, by calculating the closest distance from a series of points on the articular surface of the first implant component to the articular surface of the second implant component.

With respect to step 880, a user can adjust the angle selector 860 to any pose to adjust the gap of the representations of the implant components for the particular pose (e.g., joint flexion angle θ). For example, a user can move the angle selector 860 to a pose with approximately 90° flexion, and can move the first implant component anteriorly and/or posteriorly to contact or to be slightly gapped from the second implant component. The user can adjust the angle selector 860 to any other captured flexion angle θ and make component adjustments to the representation of the first implant component (e.g., to the representation of the first implant component 804) until the representation of the first implant component is just contacting or is slightly gapped from the representation of the second implant component (or bone) throughout the entire range of motion of the joint. If, for example, the desired gap cannot be achieved by adjusting the representation of the first implant component only, the representation of the second implant component can be adjusted. Both implant components can be adjusted until they are just contacting or slightly gapped throughout the range of motion. Alternatively, only the representation of the second implant component can be adjusted. Advantageously, this ensures that the knee restoration is properly planned (e.g., that the representations of the implant components maintain the proper relationship (e.g., gap) throughout the range of motion), which ensures the joint is properly supported by the implant components and maintains the a alignment postoperatively.

The first implant component should maintain a slight gap or just make contact with the second implant component throughout the range of motion (e.g., the bone should not articulate with the implant components), especially at full extension. If this does not occur, it might be necessary to increase the size of the first implant component or decrease the size of the second implant component. A user can adjust the size of the implant component via component size selector 842. For example, if the size of the component is changed, the representation of the new component size is automatically positioned in the same pose as the representation of the previous size, unless a unique preoperative plan already exists for the selected implant component size. Once the size is changed, it might be necessary to refine the component positions to better fit the bone (steps 872 and/or 874).

Figure 24:
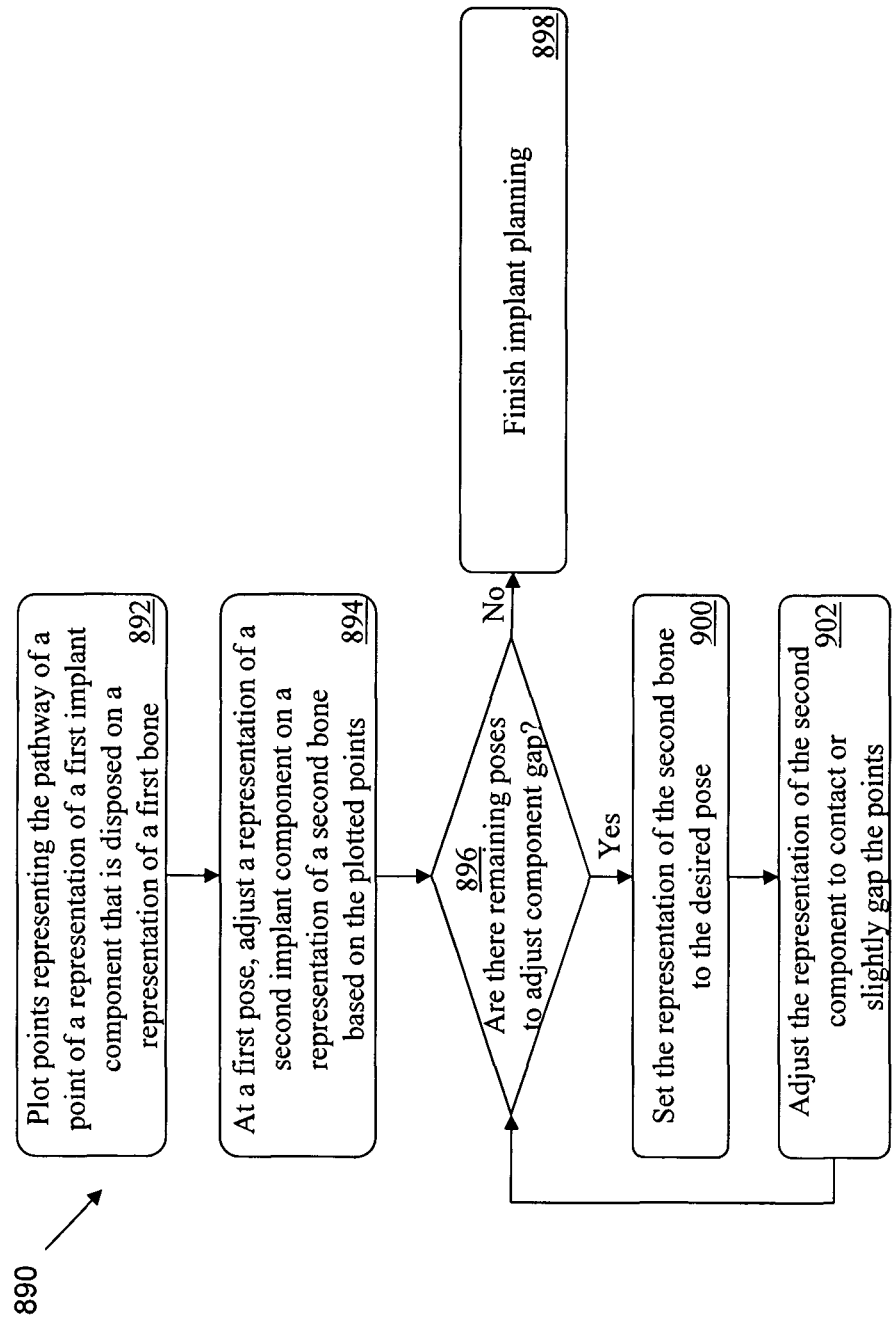
FIG. 24 illustrates an exemplary method for adjusting a distance between two representations of implant components throughout a range of motion of a joint according to another embodiment.

FIG. 24 illustrates an exemplary computerized method 890 for adjusting a distance between two representations of implant components throughout a range of motion of a joint according to another embodiment. Points are plotted (892) representing the pathway of a point of a representation of a first implant component that is disposed on a representation of a first bone. At a first pose, a representation of a second implant component on a representation of a second bone is adjusted (894) based on the plotted points. If there are no remaining poses to adjust the component gap for (896), implant planning is finished (898). If there are remaining poses to adjust the component gap for, the representation of the second bone is set (900) to the desired pose. The representation of the second component is adjusted (902) to contact or slightly gap the points.

For example, referencing FIG. 22(a), a user selects the trace points button 854. Selecting the trace points button 854 can cause the set of traced points 828 to be plotted in three dimensions in the planning sections 822. The traced points 828 represent, for example, the pathway of the articular center point of the representation of the tibial implant component 826A throughout the range of motion. Optionally, one or more anterior dots (which can be color coded, such as orange, for easy identification) can represent the anterior articular surface of the representation of the tibial implant component 826A at full extension. Similarly, one or more posterior dots (which can also be color coded) can represent the posterior articular surface of the representation of the tibial implant component 826A at full flexion. The entire set of traced points 828 shows the full extent of the representation of the tibia 824A range of motion from full extension to full flexion, providing visual guidance for positioning the representation of the femoral component (e.g., the representation of the second implant component 806). The representation of the femoral implant component can be adjusted to best-fit all the traced points 828, either contacting or being slightly gapped from the traced points 828 (e.g., between 0 mm and 1.25 mm). If, for example, the desired gap cannot be achieved by adjusting only the representation of the femoral implant component, the representation of the tibial implant component 826A can be adjusted. For example, a user can adjust both components until they are just contacting or slightly gapped throughout the range of motion. Alternatively, only the representation of the tibial component can be adjusted. This can ensure that the knee restoration is properly planned.

Overcorrection of the joint for the disease pathology can result in the implants remaining in contact during the range of motion with an amount of compression force (e.g., via the MCL and LCL ligaments, etc.). Sometimes it can be difficult to determine the degree of overcorrection, if any. Since a slight gap can be used to ensure there is no overcorrection, a gap between 0 mm and 1.25 mm can be used to achieve a gap just greater than zero to avoid overcorrection or overstuffing of the joint space. If, for example, under valgus stress, there is a gap between the tibial and femoral components, the knee is loose. A gap of approximately 1.0 mm can be considered an acceptable amount of looseness. If, for example, the gap is greater than 2 mm, the knee may be considered too loose. If under the appropriate valgus stress, there is no gap, then the knee is tight. If a tight knee plan were implemented, the implants would be held together tightly due to excessive soft tissue tension. On the graph of FIG. 9(a), this condition is represented as a negative gap. The bars of a negative gap can be color coded for easy identification, such as with an orange bar.

Both methods 870 and 890 allow planning of flexion and extension gaps of the implant components that are, for example, substantially equal or within a desired range. A distance between representations of implant components and/or representations of bones can be preserved (e.g., maintained within a desired range, such as between 0 mm to 1.25 mm, or at a desired value, such as approximately 1 mm) through at least a portion of the range of motion of the joint. Correct gaps results in properly tensioned ligaments of the joint. Different implant planning locations influence the gap/overlap at different poses. For example, in extension, the femoral component proximal/distal motion is the motion that is most related to the gap/overlap condition. In some examples, in flexion, the femoral component anterior/posterior motion is the motion that is most related to the gap/overlap condition. Graph 600 of FIG. 9(a) can be used to combine, in one display, the effects of implant placement for all captured poses. Each bar can represent implant overlap (i.e., knee tightness) or implant gap (i.e., knee looseness) at a specific knee pose (or flexion angle $\theta$). For example, for each of the captured poses of the range of motion of the joint, a bar is displayed that indicates a relationship between the pose and a distance between an implant model and a representation of a corresponding implant component and/or a corresponding representation of a bone. For example, the bar indicates the relationship between the pose and a distance between the representation of the first implant component 804 and the representation of the second bone 802 and/or the representation of the second implant component 806. Since all poses are represented in one graph, while planning in one specifically chosen pose, the effects on other poses can be simultaneously observed and considered.

For example, in a preferred embodiment, bone poses are captured at four joint flexion angles (e.g., 10°, 40°, 60°, and 90°), four gap values are calculated, and four bars are displayed on a graph similar to the graph 600 shown in FIG. 9(a). For example, as shown in FIG. 21(a), a graph can be displayed showing the four bars. To achieve an implant plan where the joint is suitably gapped at each flexion angle θ, the surgeon can adjust the position and/or orientation of the representations of the implant components as desired. In some examples, adjustments made in flexion may affect extension and vice versa. A user (e.g., surgeon) can, for example, when adjusting an implant component at a first flexion angle θ (e.g., using the implant planning display of FIGS. 22(a)-22(c)), check for possible effects of the adjustment in other flexion angles. For example, each time a representation of an implant is adjusted, the gap or overlap value for the two measured points at each pose 954 is recalculated, and the graph 950 shown in FIG. 21(a) can be updated so the surgeon can see the impact of the adjustment at each displayed flexion angle θ (e.g., each measured pose 954). For example, if an adjustment to the one or more implants causes a gap of 0.5 mm at the pose 954D (i.e., the joint flexion angle θ=90°), the graph 950 updates the bar 956D to extend from 0.0 mm to 0.5 mm in the positive direction. In another example, to create a gap instead of the overlap as indicated by the bar 956D for pose 954D, the user can decrease tightness through an anterior translation of the representation of the femoral condyle implant component. If the anterior translation causes the gap or overlap of any of the other poses (i.e., poses 954A, 954B, and 954C) to change, the bars 956 are updated to reflect the new gap/overlap values. Advantageously, because the entire graph 950 can be updated each time one or more implant components are adjusted, the flexion and/or extension gaps or overlaps can be planned to desired post-surgical values throughout the entire range of motion 952.

By capturing the pose of the bones of the joint (e.g., of the femur and tibia of a knee) in an appropriate relative alignment with proper ligament tensioning (e.g., the ACL and MCL), implants can be planned to be placed in a way that makes up for the disease pathology (e.g., the loss of bone and/or cartilage) and restores healthy joint kinematics. Bone pose data is captured with a corrective force applied to appropriately tension the ligaments and align the limb in a desired alignment (i.e., the desired post-implantation alignment), the implants are planned based on the corrected bone pose data to interact properly (e.g., to have a gap of between about 0 mm to about 1.25 mm) throughout the captured range of motion of the joint, and the bone resections are performed according to the plan. Implementation of the surgical plan (e.g., bone cuts or resections) can be performed using a tactile guided robotic arm as described in U.S. patent application Ser. No. 11/357,197, filed Feb. 21, 2006, published as Pub. No. 2006/0142657 on Jun. 29, 2006, and hereby incorporated by reference herein in its entirety. In a preferred embodiment, the tactile guided robotic arm is the TACTILE GUIDANCE SYSTEM™ or the RIO™, manufactured by MAKO Surgical Corp., Fort Lauderdale, Fla.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites.

Method steps can be performed by one or more processors executing a computer program to perform functions of the invention by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit). Subroutines can refer to portions of the computer program and/or the processor/special circuitry that implement one or more functions.

Processors suitable for the execution of a computer program include, by way of example, both general and special purpose microprocessors, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Information carriers suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computer in communication with a display device, e.g., a CRT (cathode ray tube), plasma, or LCD (liquid crystal display) monitor, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The computing system can include clients and servers. A client and a server are generally remote from each other and typically interact through a communication network. The relationship of client and server arises by virtue of computer programs running on the respective computers and having a client-server relationship to each other.

The components of the computing system can be interconnected by any form or medium of digital or analog data communication (e.g., a communication network). Examples of communication networks include circuit-based and packet-based networks. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

Devices of the computing system can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). Mobile computing device include, for example, a Blackberry®. IP phones include, for example, a Cisco® Unified IP Phone 7985G available from Cisco System, Inc, and/or a Cisco® Unified Wireless Phone 7920 available from Cisco System, Inc.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A surgical planning method comprising:
   tracking, using a tracking system, a first position tracker affixed to a first bone of a native joint while the first bone, a second bone, or both bones of the native joint are subject to a corrective force aligning the first and second bones in a desired alignment;
   capturing pose data, obtained from the first position tracker, of the native joint subject to the corrective force at a plurality of poses within a range of motion of the native joint, the data representative of a corrected limb pose at the plurality of poses within the range of motion of the native joint;
   using the computing system to:
      represent the first bone of the joint;
      represent the second bone of the joint;
      associate a first implant model with the representation of the first bone;
      associate a second implant model with the representation of the second bone;
      based on the captured data, determine, an amount of an overlap between the first implant model and the second implant model at one or more poses of the plurality of poses within the range of motion of the joint; and
   displaying on a display device information representative of the determined amount of the overlap.

2. The method of claim 1 wherein the desired alignment is based on a mechanical axis of the first and second bones, an anatomic axis of the first bone, an anatomic axis of the second bone, a tension of one or more ligaments associated with the joint, or any combination thereof.

3. The method of claim 1 further comprising applying the corrective force to induce a moment on the joint, the induced moment correcting a tension of one or more ligaments associated with the joint.

4. The method of claim 3 further comprising, prior to applying the corrective force, surgically neutralizing an influence of one or more defects of the joint associated with a disease pathology, wherein the one or more defects prevent the first and second bones from achieving the desired alignment.

5. The method of claim 4 wherein the disease pathology comprises osteoarthritis and the one or more defects comprises an osteophyte, a capsular adhesion, an osteochonral defect, or any combination thereof.

6. The method of claim 1 wherein the plurality of poses comprises a full extension of the joint, a full flexion of the joint, a pose of the joint between full extension and full flexion, or any combination thereof.

7. The method of claim 1 further comprising:
   applying a corrective force of a first magnitude at a first pose of the plurality of poses to correct a tension of one or more ligaments associated with the joint; and
   applying a corrective force of a second magnitude at a second pose of the plurality of poses to correct the tension of the one or more ligaments.

8. The method of claim 1 wherein the displaying the information comprises displaying, for one or more poses of the plurality of poses within the range of motion of the joint, a relationship between the pose and a distance between the first implant model and the second implant model.

9. The method of claim 8 wherein the distance is a gap between the first implant model and the second implant model, an overlap of the first implant model and the second implant model, or both.

10. The method of claim 8 wherein displaying comprises displaying one or more points, one or more bar graphs, one or more pie charts, a measured quantity, a value, or any combination thereof.

11. The method of claim 1 further comprising enabling a user to change a pose of the first implant model, a pose of the second implant model, or both.

12. The method of claim 11 wherein enabling comprises enabling the user to change the pose of the first implant model, the pose of the second implant model, or both to preserve a distance between the first implant model and the second implant model through at least a portion of the range of motion of the joint.

13. The method of claim 12 wherein preserving the distance comprises maintaining the distance in a desired range.

14. The method of claim 13 wherein the desired range is a range between 0 mm to 1.25 mm, inclusive.

15. The method of claim 1 further comprising enabling a user to select a third implant model with a different size than the first implant model, wherein the third implant model is automatically associated with the representation of the first bone at a position of the first implant model.

16. The method of claim 1 further comprising:
mapping at least one point on a surface of the first implant model at a plurality of poses within the range of motion of the joint, inclusive; and
aligning at least one of the mapped points with the second implant model.

17. The method of claim 1 further comprising enabling a user to change a pose of at least one of the first implant model and the second implant model to preserve a distance between the first implant model and the second implant model through at least a portion of the range of motion of the joint.

18. The method of claim 1 further comprising adjusting a pose of at least one of the first implant model and the second implant model to achieve a desired relationship between the first implant model and the second implant model through at least a portion of the corrected range of motion of the joint.

19. A surgical planning system comprising:
a tracking system, comprising a first position tracker configured to be affixed to a first bone of a native joint; and
a computer configured to:
track, using the tracking system, the first position tracker while the first bone, a second bone, or both bones of the native joint are subject to a corrective force aligning the first and second bones in a desired alignment;
capture pose data, obtained by tracking the first position tracker, of the native joint subject to the corrective force at a plurality of poses within a range of motion of the native joint, representative of a corrected limb pose at the plurality of poses within the range of motion of the native joint;
represent the first bone of the joint;
represent the second bone of the joint;
associate a first implant model with the representation of the first bone;
associate a second implant model with the representation of the second bone;
based on the captured data, determine an amount of an overlap between the first implant model and the second implant model at one or more poses of the plurality of poses within the range of motion of the joint; and
display information representative of the determined amount of the overlap.

20. The surgical computing system of claim 19 wherein the computer is further configured to enable a user to change a pose of at least one of the first implant model and the second implant model to preserve a distance between the first implant model and the second implant model through at least a portion of the range of motion of the joint.

21. The surgical computing system of claim 20 wherein preserving the distance comprises maintaining the distance in a desired range.

22. The surgical computing system of claim 19 wherein the computer is further configured to:
based on the captured data, determine a relationship between the first implant model and the second implant model through at least a portion of the range of motion of the joint; and
generate a user interface that enables a user to select a pose at which the determined relationship is calculated, displayed, or both.

23. A computer program product, tangibly embodied in a non-transitory computer readable medium, the computer program product including instructions being operable to cause a data processing apparatus to:
capture pose data of a native joint, obtained from a first position tracker affixed to a first bone of the native joint, while the first bone, a second bone, or both bones of the native joint are subject to a corrective force aligning the first and second bones in a desired alignment, the data captured at a plurality of poses within a range of motion of the native joint, representative of a corrected limb pose at the plurality of poses within the range of motion of the native joint;
represent the first bone of the joint;
represent the second bone of the joint;
associate a first implant model with the representation of the first bone;
associate a second implant model with the representation of the second bone;
based on the captured data, determine an amount of at least one of a gap or an overlap between the first implant model and the second implant model at one or more poses of the plurality of poses within the range of motion of the joint; and
display information representative of the determined amount of at least one of the gap or the overlap.

24. A system comprising:
means for tracking a first position tracker affixed to a first bone of a native joint while the first bone, a second bone, or both bones of the native joint are subject to a corrective force aligning the first and second bones in a desired alignment;
means for capturing, from the means for tracking, pose data of the native joint subject to the corrective force at a plurality of poses within a range of motion of the native joint, representative of a corrected limb pose at the plurality of poses within the range of motion of the native joint;
means for representing the first bone of the joint;
means for representing the second bone of the joint;
means for associating a first implant model with the representation of the first bone;
means for associating a second implant model with the representation of the second bone;
based on the captured data, means for determining an amount of at least one of the gap or the overlap between the first implant model and the second implant model at one or more poses of the plurality of poses within the range of motion of the joint; and
means for displaying information representative of the determined amount of at least one of the gap or the overlap.

* * * * *